US012622936B2

(12) United States Patent
Yun et al.

(10) Patent No.: US 12,622,936 B2
(45) Date of Patent: May 12, 2026

(54) ANTI-TUMOR COMPOSITION

(71) Applicant: GENEMEDICINE CO., LTD., Seoul (KR)

(72) Inventors: Chae Ok Yun, Seoul (KR); Eon Ju Oh, Seoul (KR)

(73) Assignee: GENEMEDICINE CO., LTD., Seoul (KR)

( * ) Notice: Subject to any disclaimer, the term of this patent is extended or adjusted under 35 U.S.C. 154(b) by 1263 days.

(21) Appl. No.: 17/258,581

(22) PCT Filed: Jul. 10, 2019

(86) PCT No.: PCT/KR2019/008514
§ 371 (c)(1),
(2) Date: Jan. 7, 2021

(87) PCT Pub. No.: WO2020/013617
PCT Pub. Date: Jan. 16, 2020

(65) Prior Publication Data
US 2021/0386806 A1     Dec. 16, 2021

(30) Foreign Application Priority Data
Jul. 10, 2018     (KR) ........................ 10-2018-0079752

(51) Int. Cl.
| | |
|---|---|
| *A61K 35/761* | (2015.01) |
| *A61K 38/20* | (2006.01) |
| *A61P 35/00* | (2006.01) |
| *C12N 15/113* | (2010.01) |
| *C12N 15/86* | (2006.01) |

(52) U.S. Cl.
CPC .......... *A61K 35/761* (2013.01); *A61K 38/208* (2013.01); *A61P 35/00* (2018.01); *C12N 15/1136* (2013.01); *C12N 15/86* (2013.01)

(58) Field of Classification Search
CPC .................................................. A61K 35/761
See application file for complete search history.

(56) References Cited

U.S. PATENT DOCUMENTS

| | | | |
|---|---|---|---|
| 7,872,117 B2 * | 1/2011 | Shinomiya | C12N 15/1135 435/320.1 |
| 10,849,987 B2 * | 12/2020 | Yun | A61K 47/595 |
| 2007/0232555 A1 | 10/2007 | Shinomiya et al. | |
| 2013/0023578 A1 * | 1/2013 | Kim | A61P 35/00 435/375 |
| 2018/0369417 A1 | 12/2018 | Yun et al. | |

FOREIGN PATENT DOCUMENTS

| | | |
|---|---|---|
| EP | 3329934 | 6/2018 |
| KR | 10-0896483 | 5/2009 |
| KR | 10-2011-0079529 | 7/2011 |
| KR | 10-2017-0027669 | 3/2017 |
| WO | 2011/110642 | 9/2011 |

OTHER PUBLICATIONS

Ahn, H. M., et al., 2016, Oncolytic adenovirus coexpressing interleukin-12 and shVEGF restores antitumor immune function and enhances antitumor efficacy, Oncotarget 7(51):84965-84980.*
Wang, Z.-X., et al., 2011, Adenovirus-mediated siRNA targeting c-Met inhibits proliferation and invasion of small-cell lung cancer (SCLC) cells, J. Surg. Res. 171:127-135.*
Lee, Y.-S., et al., Oct. 2006, Enhanced antitumor effect of oncolytic adenovirus expressing interleukin-12 and B-7-1 in an immunocompetent murine model, Clin. Cancer Res. 12(19):5859-5856.*
Koo, T., et al., May 2017, Selective disruption of an oncogenic mutant allele by CRISPR/Cas9 induces efficient tumor regression, Nuc. Acids Res. 45(13):7897-7908.*
Hiscox, Stephen et al. "Inhibition of cancer cell motility and invasion by interleukin-12" PLOS Biology, Rapid Science Publishers, vol. 13, No. 5, Jan. 1, 1995, pp. 396-404.
Lee, J.S. Adenovirus expressing dual c-Met-specific shRNA exhibits potent antitumor effect through autophagic cell death accompanied by senescene-like phenotypes in glioblastoma cells, Oncotarget, Feb. 17, 2015, 6, 6, 4051-4065, 1-3.

* cited by examiner

*Primary Examiner* — Jeffrey S Parkin
(74) *Attorney, Agent, or Firm* — Casimir Jones, S.C.; Robert A. Goetz

(57) ABSTRACT
The present invention relates to an oncolytic adenovirus capable of co-expressing interleukin-12 and a C-met-inhibiting oligonucleotide; and an antitumor immune-boosting composition and anticancer composition comprising the oncolytic adenovirus. The present invention has first identified an adenovirus system having simultaneous effects of IL-12 expression and C-met inhibition in cancer gene treatment. The adenovirus system of the present invention is capable of inhibiting C-met while expressing interleukin-12, thereby restoring immune functions in a tumor environment to enhance anticancer effects such as the inhibition of tumor recurrence and tumor growth and to inhibit tumor migration. Accordingly, the adenovirus system of the present invention can be effectively used in the treatment of cancer.

13 Claims, 11 Drawing Sheets
Specification includes a Sequence Listing.

【FIG. 1】
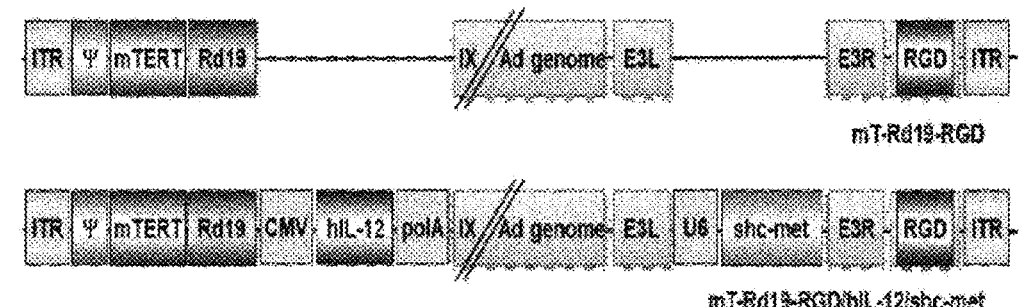
【FIG. 2】
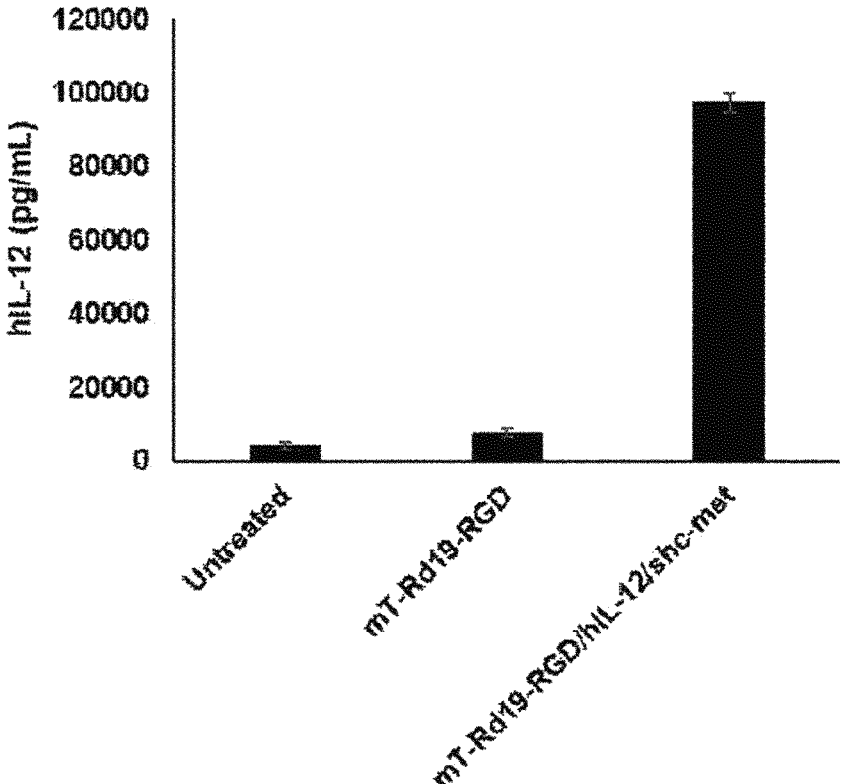

【FIG. 3】

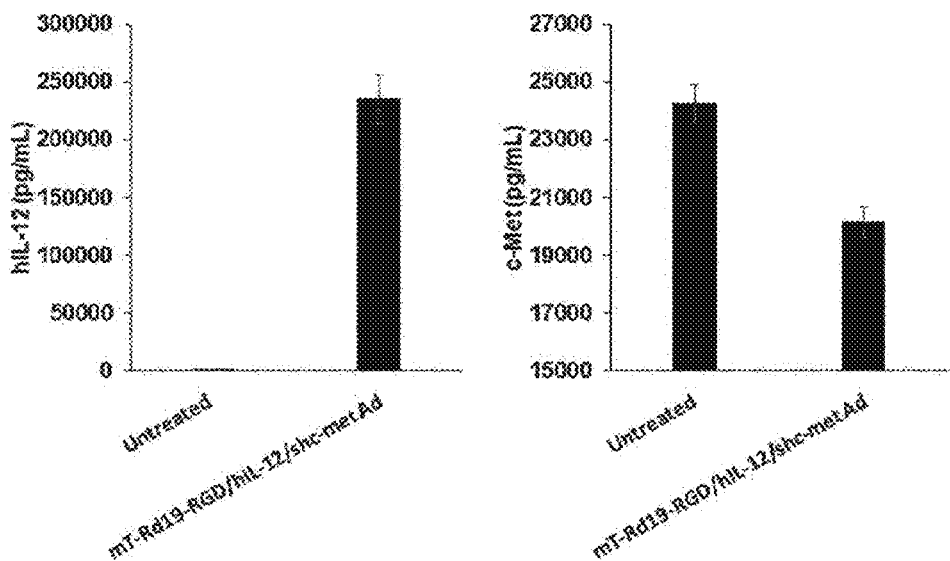

【FIG. 4】

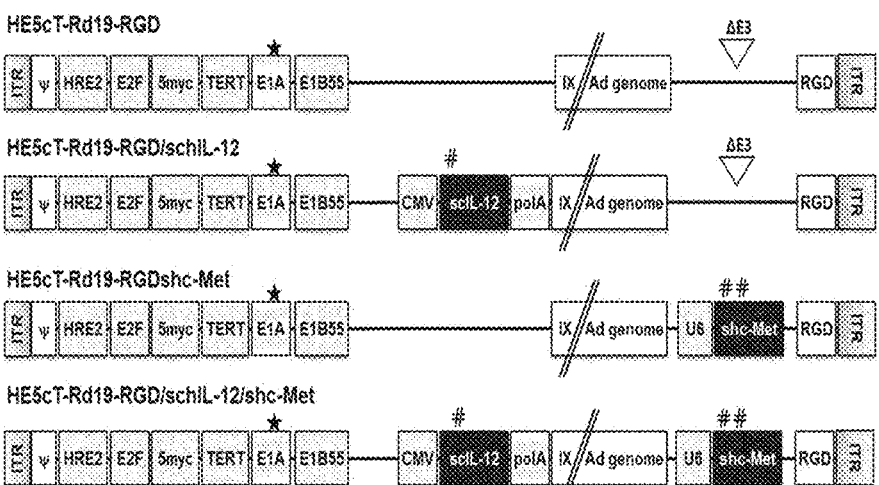

'HscIL-12' is a gene expressing human-derived IL-12
'Hshc-Met' is a gene expressing shRNA for targeting human-derived c-Met
★ Having a mutation wherein 45th Glu residue of a nucleotide sequence
encoding an Rb binding site located in EIA gene sequence is substituted with Gly,
and a mutation wherein the 121-127th amino acid sequence thereof is entirely
substituted with Gly 【FIG. 5a】
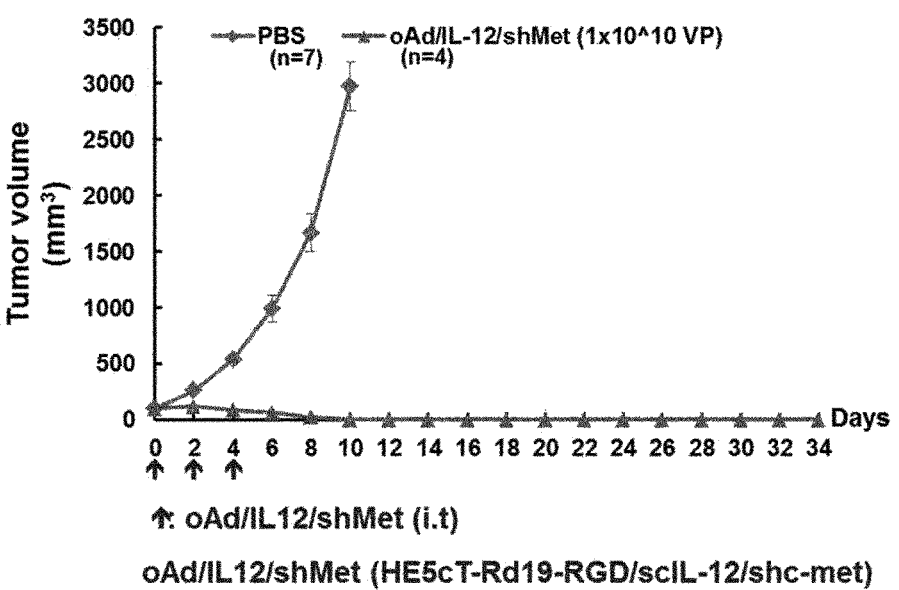
B16-F10
subcutaneous mouse melanoma model
↑: oAd/IL12/shMet (i.t)
oAd/IL12/shMet (HE5cT-Rd19-RGD/scIL-12/shc-met)
【FIG. 5b】
CT26
subcutaneous mouse colon cancer model
↑: oAd/IL12/shMet (i.t)
oAd/IL12/shMet (HE5cT-Rd19-RGD/scIL-12/shc-met)

【FIG. 6】
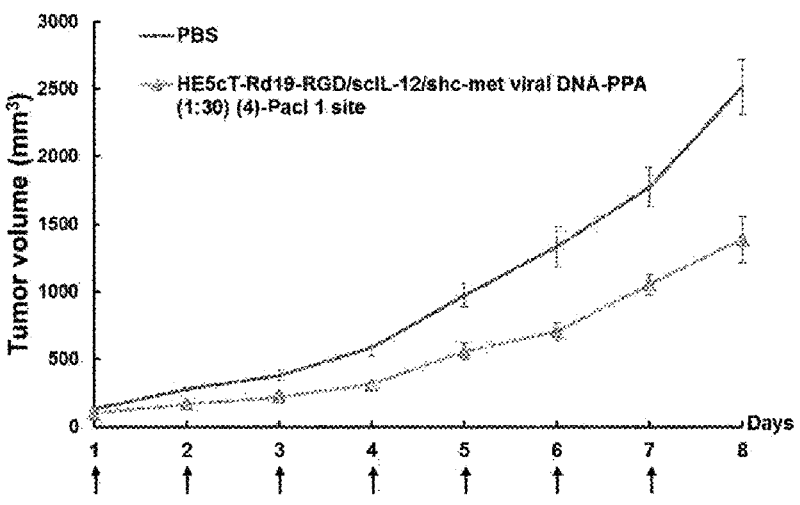
【FIG. 7a】
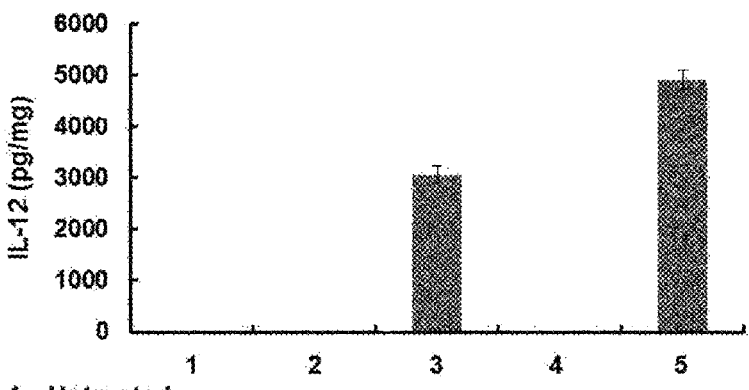
1. Untreated
2. HE5cT-Rd19-RGD          3. HE5cT-Rd19-RGD/HsclL-12
4. HE5cT-Rd19-RGD/Hshc-met  5. HE5cT-Rd19-RGD/HsclL-12/Hshc-met 【FIG. 7b】
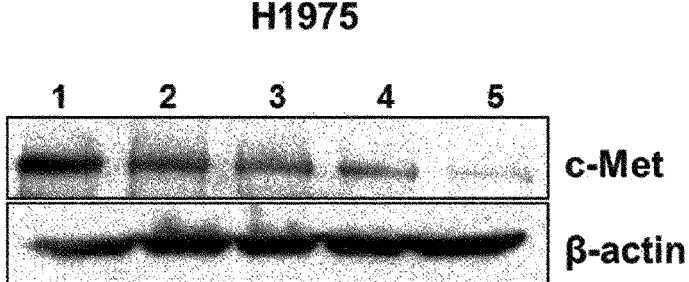
H1975
c-Met
β-actin
1. Untreated
2. HE5cT-Rd19-RGD
3. HE5cT-Rd19-RGD/HscIL-12
4. HE5cT-Rd19-RGD/Hshc-met
5. HE5cT-Rd19-RGD/HscIL-12/Hshc-met
【FIG. 8a】
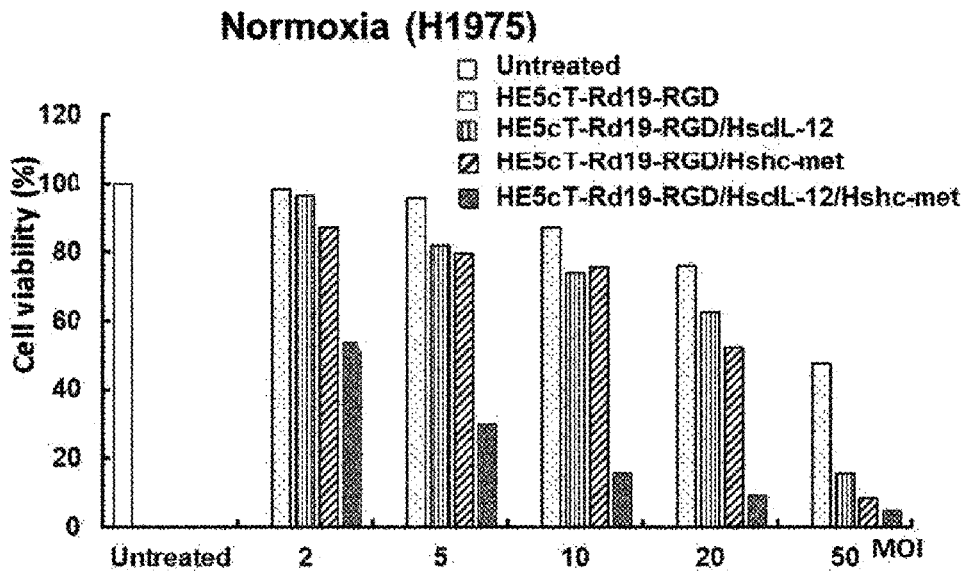
Normoxia (H1975)

【FIG. 8b】
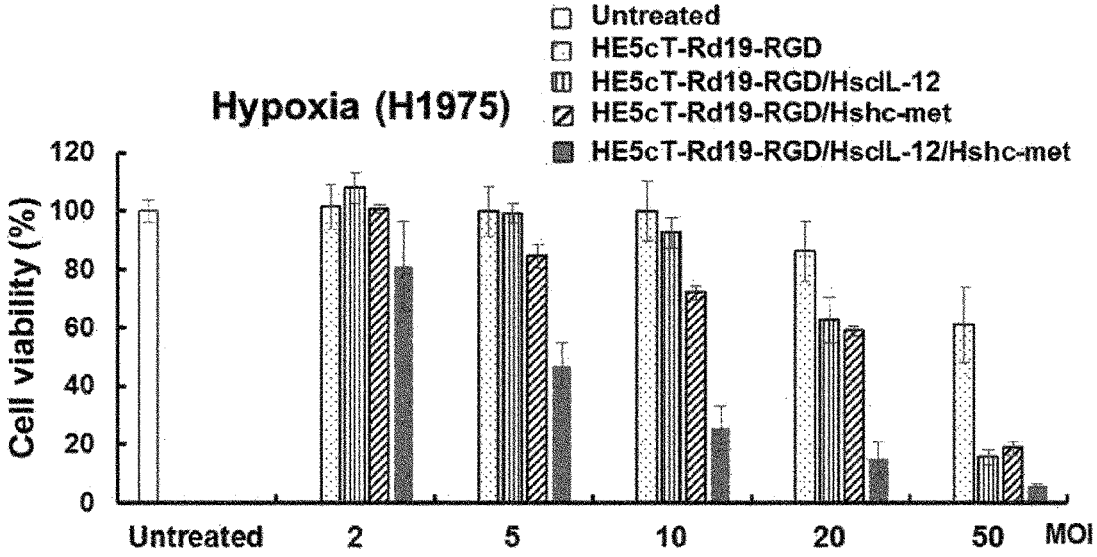
【FIG. 9a】
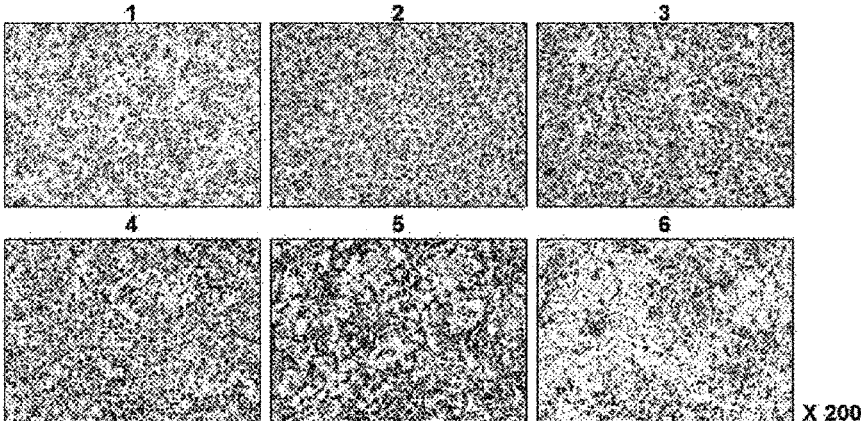
X 200
1. 5% FBS RPMI (fresh media)
2. H1975-culture media (H1975-CM)
3. HE5cT-Rd19-RGD infection H1975-CM
4. HE5cT-Rd19-RGD/HscIL-12 infection H1975-CM
5. HE5cT-Rd19-RGD/Hshc-Met infection H1975-CM
6. HE5cT-Rd19-RGD/HscIL-12/Hshc-Met infection H1975-CM 【FIG. 9b】

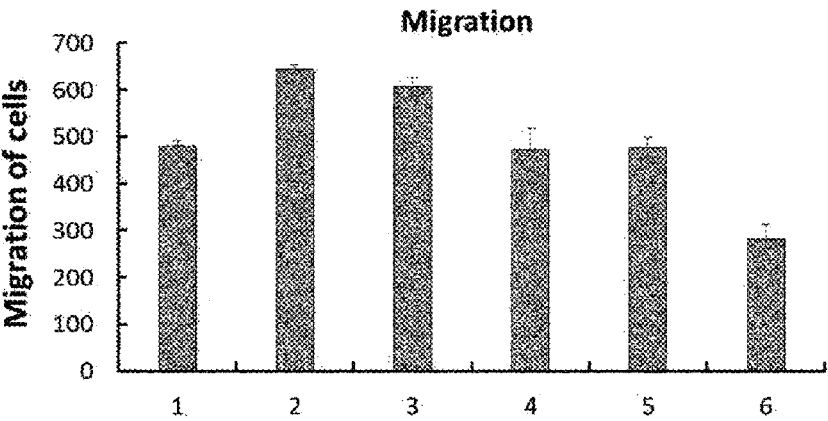

1. 5% FBS RPMI (fresh media)
2. H1975-culture media (H1975-CM)
3. HE5cT-Rd19-RGD infection H1975-CM
4. HE5cT-Rd19-RGD/HscIL-12 infection H1975-CM
5. HE5cT-Rd19-RGD/Hshc-Met infection H1975-CM
6. HE5cT-Rd19-RGD/HscIL-12/Hshc-Met infection H1975-CM 【FIG. 9c】

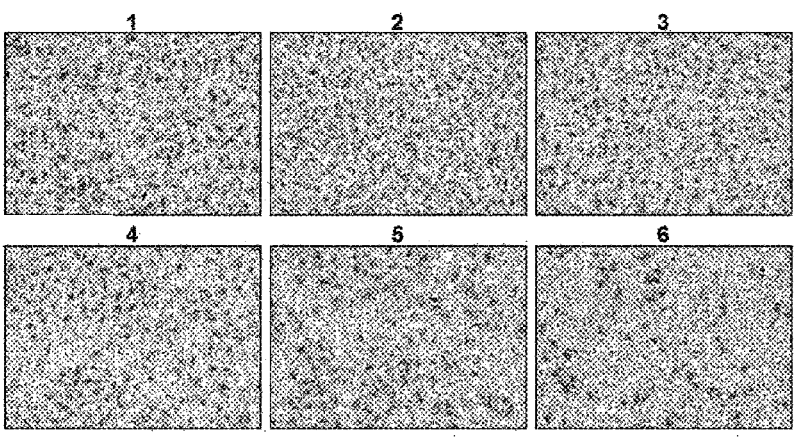

X 200

1. 5% FBS RPMI (fresh media)
2. H1975-culture media (H1975-CM)
3. HE5cT-Rd19-RGD infection H1975-CM
4. HE5cT-Rd19-RGD/HscIL-12 infection H1975-CM
5. HE5cT-Rd19-RGD/Hshc-Met infection H1975-CM
6. HE5cT-Rd19-RGD/HscIL-12/Hshc-Met infection H1975-CM 【FIG. 9d】

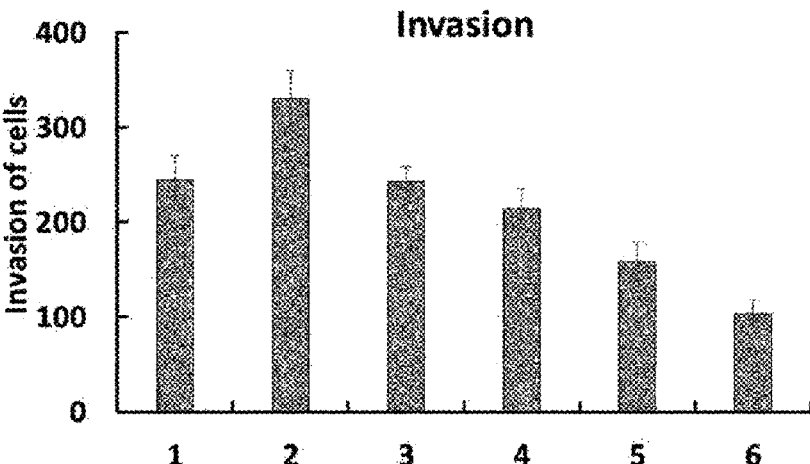

1. 5% FBS RPMI (fresh media)
2. H1975-culture media (H1975-CM)
3. HE5cT-Rd19-RGD infection H1975-CM
4. HE5cT-Rd19-RGD/HscIL-12 infection H1975-CM
5. HE5cT-Rd19-RGD/Hshc-Met infection H1975-CM
6. HE5cT-Rd19-RGD/HscIL-12/Hshc-Met infection H1975-CI

【FIG. 10】

Endothelial marker: CD31
Mesenchymal marker: α-SMA, N-cadherin

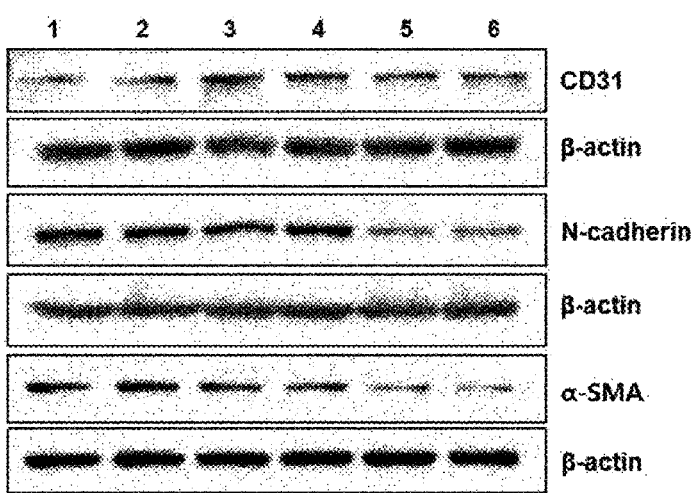

1. 5% FBS RPMI
2. H1975-culture media (H1975-CM)
3. HE5cT-Rd19-RGD infection H1975-CM
4. HE5cT-Rd19-RGD/HscIL-12 infection H1975-CM
5. HE5cT-Rd19-RGD/Hshc-Met infection H1975-CM
6. HE5cT-Rd19-RGD/HscIL-12/Hshc-Met infection H1975-CM 【FIG. 11】
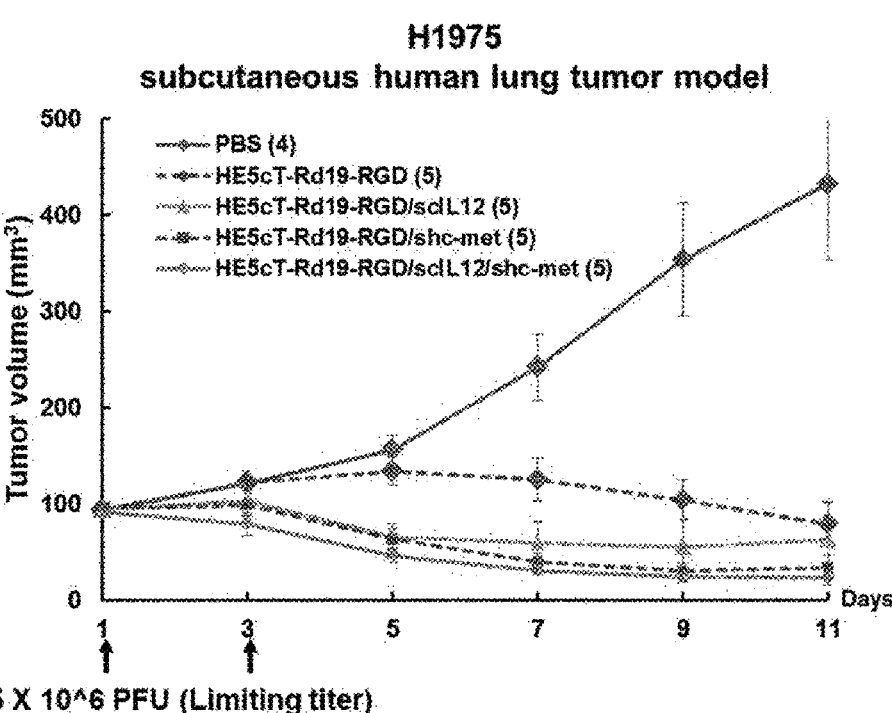
【FIG. 12】
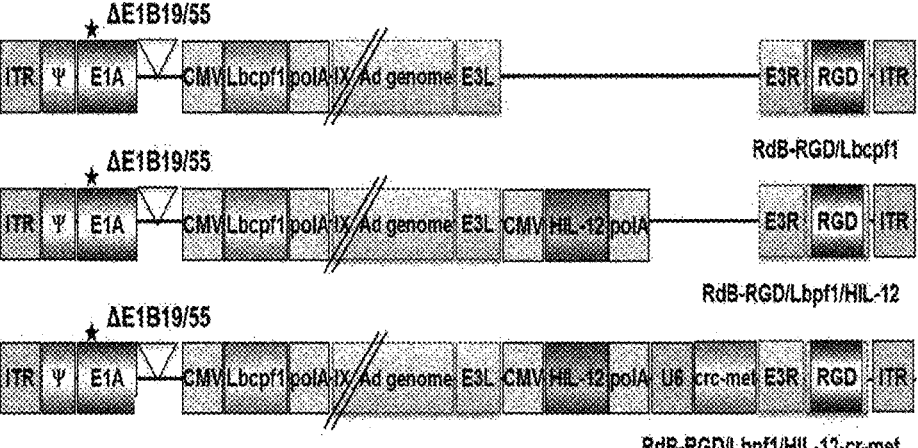
★ Having a mutation wherein 45th Glu residue of a nucleotide sequence encoding an Rb binding site located in EIA gene sequence is substituted with Gly, and a mutation wherein the 121-127th amino acid sequence thereof is entirely substituted with Gly 【FIG. 13a】
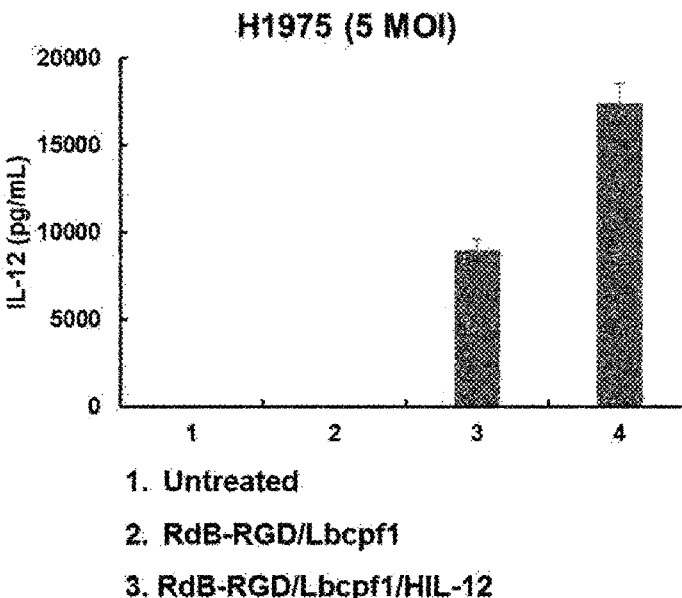
1. Untreated
2. RdB-RGD/Lbcpf1
3. RdB-RGD/Lbcpf1/HIL-12
4. RdB-RGD/Lbcpf1/HIL-12-crMET
【FIG. 13b】
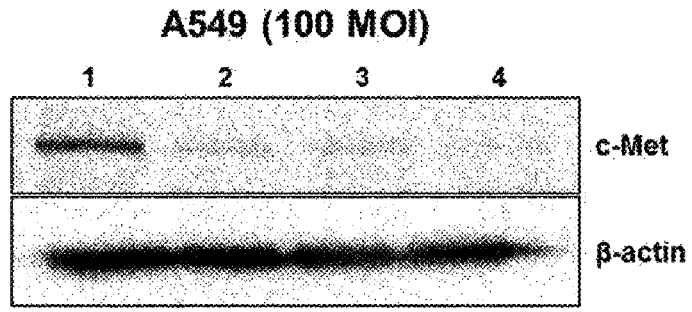
1. Untreated
2. RdB-RGD/Lbcpf1
3. RdB-RGD/Lbcpf1/HIL-12
4. RdB-RGD/Lbcpf1/HIL-12-crMET 【FIG. 13c】
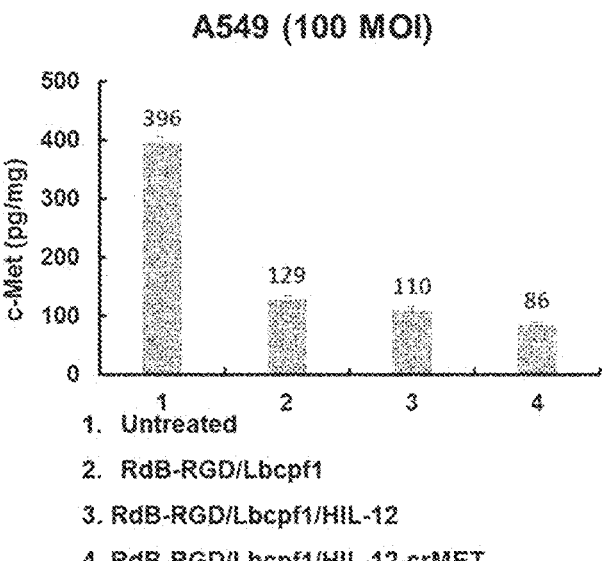
A549 (100 MOI)
1. Untreated
2. RdB-RGD/Lbcpf1
3. RdB-RGD/Lbcpf1/HIL-12
4. RdB-RGD/Lbcpf1/HIL-12-crMET
【FIG. 14】
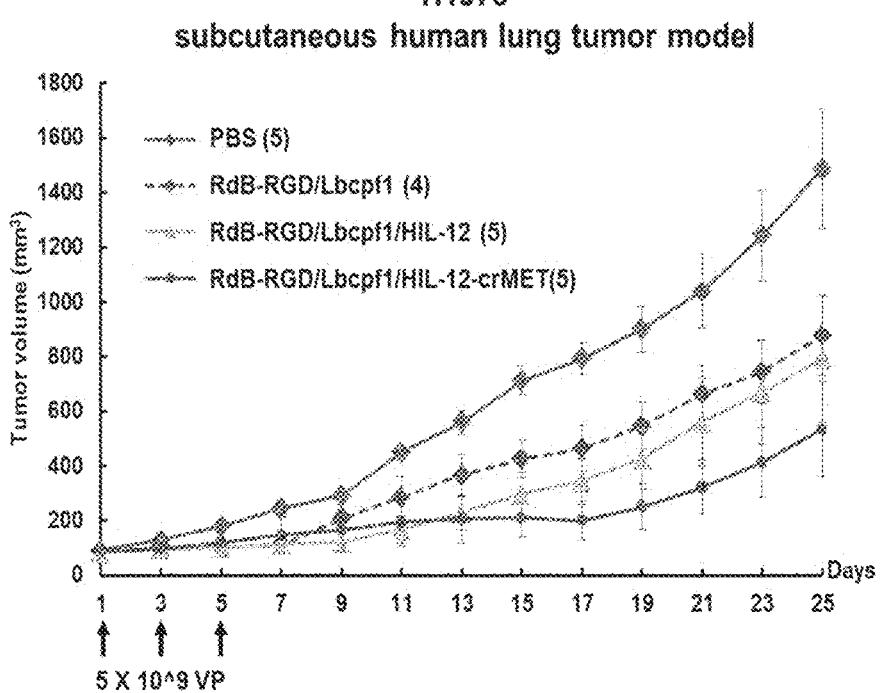
H1975
subcutaneous human lung tumor model
PBS (5)
RdB-RGD/Lbcpf1 (4)
RdB-RGD/Lbcpf1/HIL-12 (5)
RdB-RGD/Lbcpf1/HIL-12-crMET(5)
$5 \times 10^9$ VP

SEQUENCE LISTING

<160> NUMBER OF SEQ ID NOS: 20

<210> SEQ ID NO 1
<211> LENGTH: 759
<212> TYPE: DNA
<213> ORGANISM: Homo sapiens

<400> SEQUENCE: 1

```
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aattttaccc ttgcacttct     300
gaagagattg atcatgtaga tatcacaaaa gataaaacca gcacagtgga ggcctgttta     360
ccattggaat taaccaagaa tgagagttgc ctaaattcca gagagacctc tttcataact     420
aatgggagtt gcctggcctc cagaaagacc tcttttatga tggccctgtg ccttagtagt     480
atttatgaag acttgaagat gtaccaggtg gagttcaaga ccatgaatgc aaagcttctg     540
atggatccta gaggcagat cttttctagat caaaacatgc tggcagttat tgatgagctg     600
atgcaggccc tgaatttcaa cagtgagact gtgccacaaa aatcctccct tgaagaaccg     660
gatttttata aaactaaaat caagctctgc atacttcttc atgctttcag aattcgggca     720
gtgactattg atagagtgat gagctatctg aatgcttcc                            759
```

<210> SEQ ID NO 2
<211> LENGTH: 921
<212> TYPE: DNA
<213> ORGANISM: Homo sapiens

<400> SEQUENCE: 2

```
atatgggaac tgaagaaaga tgtttatgtc gtagaattgg attggtatcc ggatgcccct      60
```

-continued

```
ggagaaatgg tggtcctcac ctgtgacacc cctgaagaag atggtatcac ctggaccttg      120
gaccagagca gtgaggtctt aggctctggc aaaaccctga ccatccgagt caaagagttt      180
ggagatgctg gccagtacac ctgtcacaaa ggaggcgagg ttctaagcca ttcgctcctg      240
ctgcttcaca aaaaggaaga tggaatttgg tccactgata tttttaaagga ccagaaagaa      300 cccaaaaata agacctttct aagatgcgag gccaagaatt attctggacg tttcacctgc      360
tggtggctga cgacaatcag tactgatttg acattcagtg tcaaaagcag cagaggctct      420
tctgaccccc aagggggtgac gtgcggagct gctacactct ctgcagagag agtcagaggg      480
gacaacaagg agtatgagta ctcagtggag tgccaggagg acagtgcctg cccagctgct      540
gaggagagtc tgcccattga ggtcatggtg gatgccgttc acaagctcaa gtatgaaaac      600
tacaccagca gcttcttcat cagggacatc atcaaacctg acccacccaa gaacttgcag      660
ctgaagccat aaagaattc tcggcaggtg gaggtcagct gggagtaccc tgacacctgg      720
agtactccac attcctactt ctccctgaca ttctgcgttc aggtccaggg caagagcaag      780
agagaaaaga aagatagagt cttcacggac aagacctcag ccacggtcat ctgccgcaaa      840
aatgccagca ttagcgtgcg ggcccaggac cgctactata gctcatcttg gagcgaatgg      900
gcatctgtgc cctgcagtta g                                                921
```

```
<210> SEQ ID NO 3
<211> LENGTH: 1725
<212> TYPE: DNA
<213> ORGANISM: Artificial
<220> FEATURE:
<223> OTHER INFORMATION: Human IL-12 (p35-linker-p40)

<400> SEQUENCE: 3
```

```
atgtggcccc ctgggtcagc ctcccagcca ccgccctcac ctgccgcggc cacaggtctg       60
catccagcgg ctcgccctgt gtccctgcag tgccggctca gcatgtgtcc agcgcgcagc      120
ctcctccttg tggctaccct ggtcctcctg gaccacctca gtttggccag aaacctcccc      180
gtggccactc cagacccagg aatgttccca tgccttcacc actcccaaaa cctgctgagg      240
gccgtcagca acatgctcca gaaggccaga caaactctag aattttaccc cttgcacttct      300 gaagagattg tcatgtagaa tatcacaaaa gataaaacca gcacagtgga ggcctgttta      360
ccattggaat taaccaagaa tgagagttgc ctaaattcca gagagacctc tttcataact      420
aatgggagtt gcctggcctc cagaaagacc tcttttatga tggccctgtg ccttagtagt      480
atttatgaag acttgaagat gtaccaggtg gagttcaaga ccatgaatgc aaagcttctg      540
atggatccta agaggcagat ctttctagat caaaacatgc tggcagttat tgatgagctg      600
atgcaggccc tgaatttcaa cagtgagact gtgccacaaa atcctccct gaagaaccg       660 gattttata aaactaaaat caagctctgc atacttcttc atgctttcag aattcgggca      720
gtgactattg atagagtgat gagctatctg aatgcttccg gtggcggtgg ctcgggcggt      780
ggtgggtcgg gtggcggcgg atctatatgg gaactgaaga aagatgttta tgtcgtagaa      840
ttggattggt atccggatgc ccctggagaa atggtggtcc tcacctgtga caccccctgaa      900 gaagatggta tcacctggac cttggaccag agcagtgagg tcttaggctc tggcaaaacc      960
ctgaccatcc gagtcaaaga gtttggagat gctggccagt acacctgtca caaaggaggc     1020
gaggttctaa gccattcgct cctgctgctt cacaaaaagg aagatggaat ttggtccact     1080 gatatttta aggaccagaa agaacccaaa ataagacct ttctaagatg cgaggccaag      1140
```

```
aattattctg gacgtttcac ctgctggtgg ctgacgacaa tcagtactga tttgacattc      1200
agtgtcaaaa gcagcagagg ctcttctgac ccccaagggg tgacgtgcgg agctgctaca      1260
ctctctgcag agagagtcag aggggacaac aaggagtatg agtactcagt ggagtgccag      1320
gaggacagtg cctgcccagc tgctgaggag agtctgccca ttgaggtcat ggtggatgcc      1380
gttcacaagc tcaagtatga aaactacacc agcagcttct tcatcaggga catcatcaaa      1440
cctgacccac ccaagaactt gcagctgaag ccattaaaga attctcggca ggtggaggtc      1500
agctgggagt accctgacac ctggagtact ccacattcct acttctccct gacattctgc      1560
gttcaggtcc agggcaagag caagagagaa aagaaagata gagtcttcac ggacaagacc      1620
tcagccacgg tcatctgccg caaaaatgcc agcattagcg tgcgggccca ggaccgctac      1680
tatagctcat cttggagcga atgggcatct gtgccctgca gttag                     1725
```

<210> SEQ ID NO 4
<211> LENGTH: 762
<212> TYPE: DNA
<213> ORGANISM: Homo sapiens

<400> SEQUENCE: 4

```
atgtggcccc ctgggtcagc ctcccagcca ccgccctcac ctgccgcggc cacaggtctg        60
catccagcgg ctcgccctgt gtccctgcag tgccggctca gcatgtgtcc agcgcgcagc       120
ctcctccttg tggctaccct ggtcctcctg gaccacctca gtttggccag aaacctcccc       180
gtggccactc cagacccagg aatgttccca tgccttcacc actcccaaaa cctgctgagg       240
gccgtcagca acatgctcca gaaggccaga caaactctag aattttaccc ttgcacttct       300
gaagagattg atcatgaaga tatcacaaaa gataaaacca gcacagtgga ggcctgttta       360
ccattggaat taaccaagaa tgagagttgc ctaaattcca gagagacctc tttcataact       420
aatgggagtt gcctggcctc cagaaagacc tcttttatga tggccctgtg ccttagtagt       480
atttatgaag acttgaagat gtaccaggtg gagttcaaga ccatgaatgc aaagcttctg       540
atggatccta gagaggcagat cttctagat caaaacatgc tggcagttat tgatgagctg       600
atgcaggccc tgaatttcaa cagtgagact gtgccacaaa aatcctccct tgaagaaccg       660
gatttttata aaactaaaat caagctctgc atacttcttc atgctttcag aattcgggca       720
gtgactattg atagagtgat gagctatctg aatgcttcct aa                        762
```

<210> SEQ ID NO 5
<211> LENGTH: 987
<212> TYPE: DNA
<213> ORGANISM: Homo sapiens

<400> SEQUENCE: 5

```
atgtgtcacc agcagttggt catctcttgg ttttccctgg tttttctggc atctcccctc        60
gtggccatat gggaactgaa gaaagatgtt tatgtcgtag aattggattg gtatccggat       120
gcccctggag aaatggtggt cctcacctgt gacacccctg aagaagatgg tatcacctgg       180
accttggacc agagcagtga ggtcttaggc tctggcaaaa ccctgaccat ccaagtcaaa       240
gagtttggag atgctggcca gtacacctgt cacaaaggag gcgaggttct aagccattcg       300
ctcctgctgc ttcacaaaaa ggaagatgga atttggtcca ctgatatttt aaaggaccag       360
aaagaaccca aaaataagac ctttctaaga tgcgaggcca agaattattc tggacgtttc       420
acctgctggt ggctgacgac aatcagtact gatttgacat tcagtgtcaa aagcagcaga       480
ggctcttctg accccccaagg ggtgacgtgc ggagctgcta cactctctgc agagagagtc       540
```

```
agaggggaca acaaggagta tgagtactca gtggagtgcc aggaggacag tgcctgccca      600
gctgctgagg agagtctgcc cattgaggtc atggtggatg ccgttcacaa gctcaagtat      660
gaaaactaca ccagcagctt cttcatcagg gacatcatca aacctgaccc acccaagaac      720
ttgcagctga agccattaaa gaattctcgg caggtggagg tcagctggga gtaccctgac      780
acctggagta ctccacattc ctacttctcc ctgacattct gcgttcaggt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagttag                                          987

<210> SEQ ID NO 6
<211> LENGTH: 2331
<212> TYPE: DNA
<213> ORGANISM: Artificial
<220> FEATURE:
<223> OTHER INFORMATION: Human IL-12 (p35-lRES-p40)

<400> SEQUENCE: 6
atgtggcccc ctgggtcagc ctcccagcca ccgccctcac ctgccgcggc cacaggtctg       60
catccagcgg ctcgccctgt gtccctgcag tgccggctca gcatgtgtcc agcgcgcagc      120
ctcctccttg tggctaccct ggtcctcctg gaccacctca gtttggccag aaacctcccc      180
gtggccactc cagacccagg aatgttccca tgccttcacc actcccaaaa cctgctgagg      240
gccgtcagca acatgctcca gaaggccaga caaactctag aatttttaccc ttgcacttct      300 gaagagattg atcatgaaga tatcacaaaa gataaaacca gcacagtgga ggcctgttta      360
ccattggaat taaccaagaa tgagagttgc ctaaattcca gagagacctc tttcataact      420
aatgggagtt gcctggcctc cagaaagacc tcttttatga tggccctgtg ccttagtagt      480
atttatgaag acttgaagat gtaccaggtg gagttcaaga ccatgaatgc aaagcttctg      540
atggatccta agaggcagat cttttctagat caaaacatgc tggcagttat tgatgagctg      600
atgcaggccc tgaatttcaa cagtgagact gtgccacaaa aatcctccct tgaagaaccg      660 gattttttata aaactaaaat caagctctgc atacttcttc atgctttcag aattcgggca      720
gtgactattg atagagtgat gagctatctg aatgcttcct aagcccccc ccctaacgtt      780 actggccgaa gccgcttgga ataaggccgg tgtgcgtttg tctatatgtt attttccacc      840
atattgccgt cttttggcaa tgtgagggcc cggaaacctg ccctgtcctt cttgacgagc      900
attcctagct aggggtcttt ccctctcgc caaaggaatg caaggtctgt tgaatgtcgt      960
gaaggaagca gttcctctgg aagcttcttg aagacaaaca acgtctgtag cgacccttg     1020 caggcagcg aacccccac ctggcgacag gtgcctctgc ggccaaaagc cacgtgtata     1080
agatacacct gcaaaggcgg cacaacccca gtgccacgtt gtgagttgga tagttgtgga     1140
aagagtcaaa tggctctcct caagcgtatt caacaagggg ctgaaggatg cccagaaggt     1200 acccccattgt atgggatctg atctggggcc tcggtgcaca tgctttacat gtgtttagtc     1260
gaggttaaaa aaacgtctag gcccccgaa ccacgggac gtggtttcc tttgaaaaac     1320 acgatgataa tatggcccaca accaatgtgt caccagcagt tggtcatctc ttggttttcc     1380
ctggtttttc tggcatctcc cctcgtggcc atatgggaac tgaagaaaga tgtttatgtc     1440
gtagaattgg attggtatcc ggatgcccct ggagaaatgg tggtcctcac ctgtgacacc     1500
cctgaagaag atggtatcac ctggaccttg gaccagagca gtgaggtctt aggctctggc     1560
```

-continued

```
aaaaccctga ccatccaagt caaagagttt ggagatgctg gccagtacac ctgtcacaaa      1620
ggaggcgagg ttctaagcca ttcgctcctg ctgcttcaca aaaaggaaga tggaatttgg      1680
tccactgata tttaaagga ccagaaagaa cccaaaaata agacctttct aagatgcgag       1740
gccaagaatt attctggacg tttcacctgc tggtggctga cgacaatcag tactgatttg      1800
acattcagtg tcaaaagcag cagaggctct tctgaccccc aaggggtgac gtgcggagct      1860
gctacactct ctgcagagag agtcagaggg gacaacaagg agtatgagta ctcagtggag      1920
tgccaggagg acagtgcctg cccagctgct gaggagagtc tgcccattga ggtcatggtg      1980
gatgccgttc acaagctcaa gtatgaaaac tacaccagca gcttcttcat cagggacatc      2040
atcaaacctg acccacccaa gaacttgcag ctgaagccat aaagaattc tcggcaggtg       2100 gaggtcagct gggagtaccc tgacacctgg agtactccac attcctactt ctccctgaca      2160
ttctgcgttc aggtccaggg caagagcaag agagaaaaga aagatagagt cttcacggac      2220
aagacctcag ccacggtcat ctgccgcaaa aatgccagca ttagcgtgcg ggcccaggac      2280
cgctactata gctcatcttg gagcgaatgg gcatctgtgc cctgcagtta g              2331
```

```
<210> SEQ ID NO 7
<211> LENGTH: 645
<212> TYPE: DNA
<213> ORGANISM: Mus musculus

<400> SEQUENCE: 7
atgtgtcaat cacgctacct cctcttttg gccacccttg ccctcctaaa ccacctcagt        60
ttggccaggg tcattccagt ctctggacct gccaggtgtc ttagccagtc ccgaaacctg       120
ctgaagacca cagatgacat ggtgaagacg gccagagaaa aactgaaaca ttattcctgc       180
actgctgaag acatcgatca tgaagacatc acacgggacc aaaccagcac attgaagacc       240
tgtttaccac tggaactaca caagaacgag agttgcctgg ctactagaga gacttcttcc       300
acaacaagag ggagctgcct gcccccacag aagacgtctt tgatgatgac cctgtgcctt       360
ggtagcatct atgaggactt gaagatgtac cagacagagt tccaggccat caacgcagca       420
cttcagaatc acaaccatca gcagatcatt ctagacaagg gcatgctggt ggccatcgat       480
gagctgatgc agtctctgaa tcataatggc gagactctgc gccagaaacc tcctgtggga      540
gaagcagacc cttacagagt gaaaatgaag ctctgcatcc tgcttcacgc cttcagcacc       600
cgcgtcgtga ccatcaacag ggtgatgggc tatctgagct ccgcc                       645
```

```
<210> SEQ ID NO 8
<211> LENGTH: 1005
<212> TYPE: DNA
<213> ORGANISM: Mus musculus

<400> SEQUENCE: 8
tgtcctcaga agctaaccat ctcctggttt gccatcgttt tgctggtgtc tccactcatg        60
gccatgtggg agctggagaa agacgtttat gttgtagagg tggactggac tcccgatgcc       120
cctggagaaa cagtgaacct cacctgtgac acgcctgaag aagatgacat cacctggacc       180
tcagaccaga gacatggagt cataggctct ggaaagaccc tgaccatcac tgtcaaagag       240
tttctagatg ctggccagta cacctgccac aaaggaggcg agactctgag ccactcacat       300
ctgctgctcc acaagaagga aaatggaatt tggtccactg aaattttaaa aaatttcaaa       360
aacaagactt tcctgaagtg tgaagcacca aattactccg gacggttcac gtgctcatgg       420
ctggtgcaaa gaaacatgga cttgaagttc aacatcaaga gcagtagcag ttcccctgac       480
```

-continued

```
tctcgggcag tgacatgtgg aatggcgtct ctgtctgcag agaaggtcac actggaccaa      540
agggactatg agaagtattc agtgtcctgc caggaggatg tcacctgccc aactgccgag      600
gagaccctgc ccattgaact ggcgttggaa gcacggcagc agaataaata tgagaactac      660
agcaccagct tcttcatcag ggacatcatc aaaccagacc cgcccaagaa cttgcagatg      720
aagcctttga agaactcaca ggtggaggtc agctgggagt accctgactc ctggagcact      780
ccccattcct acttctccct caagttcttt gttcgaatcc agcgcaagaa agaaaagatg      840
aaggagacag aggaggggtg taaccagaaa ggtgcgttcc tcgtagagaa gacatctacc      900
gaagtccaat gcaaaggcgg gaatgtctgc gtgcaagctc aggatcgcta ttacaattcc      960
tcatgcagca agtgggcatg tgttccctgc agggtccgat cctag                     1005
```

<210> SEQ ID NO 9
<211> LENGTH: 1695
<212> TYPE: DNA
<213> ORGANISM: Artificial
<220> FEATURE:
<223> OTHER INFORMATION: Mouse IL-12 (p35-linker-p40)

<400> SEQUENCE: 9

```
atgtgtcaat cacgctacct cctctttttg gccacccttg ccctcctaaa ccacctcagt       60
ttggccaggg tcattccagt ctctggacct gccaggtgtc ttagccagtc ccgaaacctg      120
ctgaagacca cagatgacat ggtgaagacg gccagagaaa aactgaaaca ttattcctgc      180
actgctgaag acatcgatca tgaagacatc acacgggacc aaaccagcac attgaagacc      240
tgtttaccac tggaactaca caagaacgag agttgcctgg ctactagaga gacttcttcc      300
acaacaagag ggagctgcct gcccccacag aagacgtctt tgatgatgac cctgtgcctt      360
ggtagcatct atgaggactt gaagatgtac cagacagagt tccaggccat caacgcagca      420
cttcagaatc acaaccatca gcagatcatt ctagacaagg gcatgctggt ggccatcgat      480
gagctgatgc agtctctgaa tcataatggc gagactctgc gccagaaacc tcctgtggga      540
gaagcagacc cttacagagt gaaaatgaag ctctgcatcc tgcttcacgc cttcagcacc      600
cgcgtcgtga ccatcaacag ggtgatgggc tatctgagct ccgccggtgg cggtggctcg      660
ggcggtggtg ggtcgggtgg cggcggatct tgtcctcaga agctaaccat ctcctggttt      720
gccatcgttt gctggtgtc tccactcatg gccatgtggg agctggagaa agacgtttat      780
gttgtagagg tggactggac tcccgatgcc cctggagaaa cagtgaacct cacctgtgac      840
acgcctgaag aagatgacat cacctggacc tcagaccaga acatggagt cataggctct       900 ggaaagaccc tgaccatcac tgtcaaagag tttctagatg ctggccagta cacctgccac      960
aaaggaggcg agactctgag ccactcacat ctgctgctcc acaagaagga aaatggaatt     1020
tggtccactg aaattttaaa aaatttcaaa aacaagactt tcctgaagtg tgaagcacca     1080
aattactccg gacggttcac gtgctcatgg ctggtgcaaa gaaacatgga cttgaagttc     1140
aacatcaaga gcagtagcag ttcccctgac tctcgggcag tgacatgtgg aatggcgtct     1200
ctgtctgcag agaaggtcac actggaccaa agggactatg agaagtattc agtgtcctgc     1260
caggaggatg tcacctgccc aactgccgag gagaccctgc ccattgaact ggcgttggaa     1320
gcacggcagc agaataaata tgagaactac agcaccagct tcttcatcag ggacatcatc     1380
aaaccagacc cgcccaagaa cttgcagatg aagcctttga agaactcaca ggtggaggtc     1440
agctgggagt accctgactc ctggagcact ccccattcct acttctccct caagttcttt     1500
```

-continued

```
gttcgaatcc agcgcaagaa agaaaagatg aaggagacag aggaggggtg taaccagaaa    1560
ggtgcgttcc tcgtagagaa gacatctacc gaagtccaat gcaaaggcgg gaatgtctgc    1620
gtgcaagctc aggatcgcta ttacaattcc tcatgcagca agtgggcatg tgttccctgc    1680
agggtccgat cctag                                                     1695

<210> SEQ ID NO 10
<211> LENGTH: 4227
<212> TYPE: DNA
<213> ORGANISM: Homo sapiens

<400> SEQUENCE: 10
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga gagcccagcc agtgtcctg actgtgtggt gagcgccctg     540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gtttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaaagag atccacaaag aaggaagtgt ttaatatact tcaggctgcg    960
tatgtcagca gcctggggc ccagcttgct agacaaatag agccagcct gaatgatgac    1020 attcttttcg gggtgttcgc acaaagcaag ccagattctg ccgaaccaat ggatcgatct    1080
gccatgtgtg cattccctat caaatatgtc aacgacttct tcaacaagat cgtcaacaaa    1140
aacaatgtga gatgtctcca gcattttac ggacccaatc atgagcactg ctttaatagg    1200
acacttctga aaattcatc aggctgtgaa gcgcgccgtg atgaatatcg aacagagttt    1260
accacagctt gcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
```

```
tcaaatggcc acgggacaac acaatacagt acattctcct atgtggatcc tgtaataaca      1980
agtatttcgc cgaaatacgg tcctatggct ggtggcactt tacttacttt aactggaaat      2040
tacctaaaca gtgggaattc tagacacatt tcaattggtg gaaaaacatg tactttaaaa      2100
agtgtgtcaa acagtattct tgaatgttat accccagccc aaaccatttc aactgagttt      2160
gctgttaaat tgaaaattga cttagccaac cgagagacaa gcatcttcag ttaccgtgaa      2220
gatcccattg tctatgaaat tcatccaacc aaatctttta ttagtacttg gtggaaagaa      2280
cctctcaaca ttgtcagttt tctattttgc tttgccagtg gtgggagcac aataacaggt      2340
gttgggaaaa acctgaattc agttagtgtc ccgagaatgg tcataaatgt gcatgaagca      2400
ggaaggaact ttacagtggc atgtcaacat cgctctaatt cagagataat ctgttgtacc      2460
actccttccc tgcaacagct gaatctgcaa ctcccctga aaaccaaagc cttttttcatg      2520 ttagatggga tcctttccaa atactttgat ctcatttatg tacataatcc tgtgtttaag      2580
ccttttgaaa agccagtgat gatctcaatg ggcaatgaaa atgtactgga aattaaggga      2640
aatgatattg accctgaagc agttaaaggt gaagtgttaa aagttggaaa taagagctgt      2700
gagaatatac acttacattc tgaagccgtt ttatgcacgg tccccaatga cctgctgaaa      2760
ttgaacagcg agctaaatat agagtggaag caagcaattt cttcaaccgt ccttggaaaa      2820
gtaatagttc aaccagatca gaatttcaca ggattgattg ctggtgttgt ctcaatatca      2880
acagcactgt tattactact tgggtttttc ctgtggctga aaaagagaaa gcaaattaaa      2940
gatctgggca gtgaattagt tcgctacgat gcaagagtac acactcctca tttggatagg      3000
cttgtaagtg cccgaagtgt aagcccaact acagaaatgg tttcaaatga atctgtagac      3060
taccgagcta ctttttccaga agatcagttt cctaattcat ctcagaacgg ttcatgccga      3120
caagtgcagt atcctctgac agacatgtcc cccatcctaa ctagtgggga ctctgatata      3180
tccagtccat tactgcaaaa tactgtccac attgacctca gtgctctaaa tccagagctg      3240
gtccaggcag tgcagcatgt agtgattggg cccagtagcc tgattgtgca tttcaatgaa      3300
gtcataggaa gagggcattt tggttgtgta tatcatggga cttttgttgga caatgatggc      3360 aagaaaattc actgtgctgt gaaatccttg aacagaatca ctgacatagg agaagtttcc      3420
caatttctga ccgagggaat catcatgaaa gattttagtc atcccaatgt cctctcgctc      3480
ctgggaatct gcctgcgaag tgaagggtct ccgctggtgg tcctaccata catgaaacat      3540
ggagatcttc gaaatttcat tcgaaatgag actcataatc caactgtaaa agatcttatt      3600
ggctttggtc ttcaagtagc caaagcgatg aaatatcttg caagcaaaaa gtttgtccac      3660
agagacttgg ctgcaagaaa ctgtatgctg gatgaaaaat tcacagtcaa ggttgctgat      3720
tttggtcttg ccagagacat gtatgataaa gaatactata gtgtacacaa caaaacaggt      3780
gcaaagctgc cagtgaagtg gatggctttg gaaagtctgc aaactcaaaa gtttaccacc      3840
aagtcagatg tgtggtcctt tggcgtcgtc ctctgggagc tgatgacaag aggagcccca      3900
ccttatcctg acgtaaacac ctttgatata actgtttact tgttgcaagg gagaagactc      3960
ctacaacccg aatactgccc agacccctta tatgaagtaa tgctaaaatg ctggcaccct      4020
aaagccgaaa tgcgcccatc cttttctgaa ctggtgtccc ggatatcagc gatcttctct      4080
actttcattg gggagcacta tgtccatgtg aacgctactt atgtgaacgt aaaatgtgtc      4140
gctccgtatc cttctctgtt gtcatcagaa gataacgctg atgatgaggt ggacacacga      4200
ccagcctcct tctgggagac atcatag                                          4227
```

<210> SEQ ID NO 11
<211> LENGTH: 6652
<212> TYPE: DNA
<213> ORGANISM: Mus musculus

<400> SEQUENCE: 11

```
gctcggcggg gttcggcccg ggccgcaggt gacccggacg gcctcgccgc ccgcagcgtc          60
cgagcccggg tgaccctgtg cggagccaga tgctgggcga ccgctgactc gctggagaag         120
ggcggagcgc gcgggtggtc cccagccggc tgacttcggc gccgcgcgct ccgggcaccc         180
caaggtacaa actccagccg cgtcgatcag gcacccagcc tctcccagcc cctctgcttt         240
ctttgttcca ctaagggaac tggctactgc tctggaggac aagaccaccg aggatggctg         300
tggagagaaa gctgacggtg tagcagaacg cttggcatgt gatcaactcc tcacaatgaa         360
ggctcccacc gtgctggcac ctggcattct ggtgctgctg ttgtccttgg tgcagaggag         420
ccatggggag tgcaaggagg ccctagtgaa gtctgagatg aacgtgaaca tgaagtatca         480
gctccccaac ttcacggcag aaaccccat ccagaatgtc gtcctacacg gccatcatat          540
ttatctcgga gccacaaact acatttatgt tttaaatgac aaagaccttc agaaggtatc         600
cgaattcaag accgggcccg tgttggaaca cccagattgt ttaccttgtc gggactgcag         660
cagcaaagcc aattcatcag gaggggtttg gaaagacaac atcaacatgg ctctgcttgt         720
tgacacatac tatgatgatc aactcattag ctgtggcagt gtcaacagag ggacttgcca         780
gcggcatgtc cttcctcctg acaattctgc tgacatccag tctgaggtcc actgcatgtt         840
ctccccagaa gaggagtcag ggcagtgtcc tgactgtgta gtgagtgccc tcggagccaa         900
agtcctcctg tcggaaaagg accggttcat caatttcttt gtggggaata cgatcaattc         960
ctcctatcct cctggttatt cactgcattc gatatcggtg agacggctga aggaaaccca        1020
agatggtttt aagtttttga cagaccagtc ctatattgat gtcttaccag aattccaaga        1080
ttcctacccc ataaagtaca tacatgcctt cgaaagcaac catttatttt actttctgac        1140
tgtccaaaag gaaactctag atgctcagac tttcatacaa gaataatca ggttctgttc         1200 cgtagactct gggttgcact cctacatgga aatgcccctg gaatgcatcc tgacagaaaa        1260
aagaaggaag agatccacaa gggaagaagt gtttaatatc ctccaagccg cgtatgtcag        1320
taaaccaggg gccaatcttg ctaagcaaat aggagctagc ccttctgatg acattctctt        1380
cggggtgttt gcacaaagca agccagattc tgctgaacct gtgaatcgat cagcagtctg        1440
tgcattcccc atcaaatatg tcaatgactt cttcaacaag attgtcaaca aaaacaacgt        1500
gagatgtctc cagcattttt acggacccaa ccatgagcac tgtttcaata ggaccctgct        1560
gagaaactct tccggctgtg aagcgcgcag tgacgagtat cggacagagt ttaccacggc        1620
tttgcagcgc gtcgacttat tcatgggccg gcttaaccaa gtgctcctga catccatctc        1680
caccttcatc aaaggtgacc tcaccattgc taatctaggg acgtcagaag tcgcttcat         1740 gcaggtggtg ctctctcgaa cagcacacct cactcctcat gtgaacttcc tcctggactc        1800
ccatcctgta tctccagaag ttattgttga gcatccatca aatcaaaatg ctatacatt         1860 ggttgtcaca ggaaagaaga tcaccaagat tccattgaat ggcctgggct gtggacattt        1920
ccaatcctgc agtcagtgcc tctctgcccc ttactttata cagtgtggct ggtgccacaa        1980
tcaatgtgtg cgttttgatg aatgccccag cggtacatgg actcaagaga tctgtctgcc        2040
ggcggtttat aaggtgttcc ccaccagcgc gccccttgaa ggaggaacag tgttgaccat        2100
atgtggctgg gactttggat tcaggaagaa taataaattt gatttaagga aaaccaaagt        2160
```

```
tctgcttggc aacgagagct gtaccttgac cttaagcgag agcacgacaa atacgttgaa   2220
atgcacagtt ggtcccgcga tgagtgagca cttcaatgtg tctgtaatta tctcaaacag   2280
tcgagagacg acgcaataca gtgcattctc ctatgtagat cctgtaataa caagcatttc   2340
tccgaggtac ggccctcagg ctggaggcac cttactcact cttactggga aatacctcaa   2400
cagtggcaat tctagacaca tttcaattgg agggaaaaca tgtactttaa aaagtgtatc   2460
agatagtatt cttgaatgct acaccccagc ccaaactacc tctgatgagt ttcctgtgaa   2520
attgaagatt gacttggcta accgagagac cagcagcttc agttaccggg aagaccccgt   2580
tgtctatgaa atccacccga ccaaatcttt tattagtggt ggaagcacaa taacgggtat   2640
tgggaagacc ctgaactcgg ttagcctccc aaagctggta atagatgtgc atgaagtggg   2700
tgtgaactac acagtggcat gtcagcatcg ctcaaattca gagatcatct gctgcactac   2760
tccttcactg aaacagctgg gcctgcaact ccccctgaag accaaagcct tcttcctgtt   2820
agacgggatt ctttccaaac actttgatct cacttatgtg cataatcctg tgtttgagcc   2880
ttttgaaaag ccagtaatga tctcaatagg caatgaaaat gtagtggaaa ttaagggaaa   2940
caatattgac cctgaagcag ttaaaggtga agtgttaaaa gttggaaatc agagctgcga   3000
gagtctccac tggcactctg gagctgtgtt gtgtacagtc cccagtgacc tgctcaaact   3060
gaacagcgag ctaaatatag agtggaagca agcagtctct tcaactgttc ttggaaaagt   3120
gatcgttcaa ccggatcaga attttgcagg attgatcatt ggtgcggtct caatatcagt   3180
agtagttttg ttattatccg ggctcttcct gtggatgaga aagagaaagc ataaagatct   3240
gggcagtgaa ttagttcgct atgacgcaag agtacacact cctcatttgg ataggcttgt   3300
aagtgcccga agtgtaagtc caactacaga gatggtttca aatgagtctg tagactacag   3360
agctactttt ccagaagacc agtttcccaa ctcctctcag aatggagcat gcagacaagt   3420
gcaataccct ctgacagacc tgtcccctat cctgacaagt ggagactctg atatatccag   3480
cccattacta caaaatactg ttcacattga cctcagtgct ctaaatccag agctggtcca   3540
agcagttcag cacgtagtga ttggacccag cagcctgatt gtgcatttca atgaagtcat   3600
aggaagaggg cattttggct gtgtctatca tgggactttg ctggacaatg acggaaagaa   3660
aattcactgt gctgtgaaat ccttaaatag aatcacagat atagaagagg tctcccagtt   3720
tctgactgag ggaatcatca tgaaagactt cagccatccc aatgttctct cactcttggg   3780
aatctgcctg aggagtgaag ggtctcctct ggtggtcctg ccctatatga agcatggaga   3840
tctgcgaaat ttcattcgaa acgagactca taatccaact gtgaaagatc ttataggatt   3900
tggccttcaa gtagccaaag gcatgaaata tcttgccagc aaaaagtttg tccacagaga   3960
cttagctgca agaaactgca tgttggatga aaaattcact gtcaaggttg ctgatttcgg   4020
tcttgccaga gacatgtacg ataaagagta ctatagtgtc cacaacaaga cgggtgccaa   4080
gctaccagta aagtggatgg cttttagaga gtctcaaacg cagaagttca ccaccaagtc   4140
agatgtgtgg tcctttggtg tgctcctctg ggagctcatg acgagaggag ccctccttta   4200
tcccgacgtg aacacatttg atatcactat ctacctgttg caaggcagaa gactcttgca   4260
accagaatac tgtccagacg ccttgtacga agtgatgcta aaatgctggc accccaaagc   4320
ggaaatgcgc ccgtcctttt ccgaactggt ctccaggata tcctcaatct tctccacgtt   4380
cattggggaa cactacgtcc acgtgaacgc tacttatgtg aatgtaaaat gtgttgctcc   4440
atatccttct ctgttgccat cccaagacaa cattgatggc gaggggaaca catgatgaat   4500
```

```
gagaggtcca ccagcccact tccaagaaac agttctggcc caaaccagac tatcccttcc      4560
ccaacagttc tcactgcctg gcctttggaa ggtcacttaa catttgttgt tgttttgttt      4620
tgttttttgt tttgcttttg cggtaactgc accactatga aacattgact tgctatttca      4680
aattcctgga ttctaaggaa tttctcatct gacaatggaa cagaaataga agcatggccc      4740
ccacaggctg gggaccagtg gcaacctgca gctacaacac tcctatctca gcggaattct      4800
aaatctcagt tctggcttaa aagtttaaa aataagatat atatacatat atatatccaa      4860
tacaatgaac tttgaagatt tctcagaaaa ctcagaagaa acgccctctt tcaggataaa      4920
tgtggtgttc ctagcaggct gcttgttgaa attccagtgt tttaaaaata tttttgttgt      4980
gttgcagtcg tgaacatttt ccatttctga tgttgtctgc ccatcaggca aacattccct      5040
tttaaatgct tatatacaca ttccttaggt tggaagaata tccacggaca atgcacttat      5100
ttttaaacga gcatgacatg aggtgtgttt ataaattatc agggatttta tgtattgtac      5160
atagatgaca ataggaaatt gtttatttca agaaatagct ttgttacagt aaaatatttg      5220
tcatttaaaa cccagctgtt tagcaaggag tgttggctca cacctacaat cccagcattt      5280
gggaagctga ggcaagcaga ttaccacaag tttgaaacca accttggctg catacagatg      5340
atgtatatat aggccagcat gggttacact gtctgtctta gcaaacaaaa tttcaactgt      5400
ttgagaaaga ttttgttctg atctaatgaa tgtggacatt taaatttttt atctgttttt      5460
taatggcaac tttggaaata agtaacttgc ggtgataaat cttttttaaag gcaactcagt      5520 atttttttaaa ggacaaaata aactgactga agggttcgct acttccagtc acaacctgtg      5580
tatagaagaa agaaagggtc agtgatcgag aatcagacac tctcgttcag gaggaggctt      5640
ctcgcctgaa acaattgcac ccaacacttt tggggaagtc tcatttttgc attaggacat      5700
attttaggtt aaacaaaagc atattttaga aacagacaaa agccaactga aaatcgtgga      5760
tgaatagtta ctctggacag gacttttgac atgtcttgct ctgtggaatt ttgtgcttac      5820
tactgtatag tgcatgtggc ttaggttacc ctagctggtt ttgtccgtgt aaacattgaa      5880
agtattatat ttttatagaa atgtttattt ttaatgatgt aagaaaaatt ttccttaggc      5940
cgcagaaatc ctgcactgtg agcatttcag aagaggtatg tgagacccag ttcaacgaca      6000
gcatgatttt ttaaatggct gtaagttatg ataaggaaat gtactgattg ccagtgcact      6060
ccaccctcat tacgtcacca ggacttgaag ccaaggggtta agaggcaag ctatgacatg      6120 ggtgtgtggt ctgctgaaac ccaatcgttg aacttggctg ttgttacagg aaaatgatgg      6180
catcaacagg tctttgatgg tggtggagca tatcagaaca cataaggaac tgtagcccag      6240
atttatttca attcaaatat tactgcttcg taattatgaa gagtagtgca aatttacaga      6300
gcactgtcaa agactgacag aaaaaaaaaa gatctgctct gtagaaagaa ttgtctgcca      6360
ttacagggtc aagaaaatga atgcgccaat aacagtaaga gctgtggaag acacccatac      6420
ctgtatatac atgctcgaga aagctgtaat gtgaaaatca tgttctctat ttatgactct      6480
tcctagggca atgtgtctgg acagattgta agagtaagtc attttcctaa agaattagat      6540
atttgtcact gcctatacct gcagttgagc tgaatggtac tccatgtgtt aataattgtt      6600
ctgatgaatc atacagttga aataaagtga cgtaacatct tgtatactgt ga             6652
```

<210> SEQ ID NO 12
<211> LENGTH: 62
<212> TYPE: DNA
<213> ORGANISM: Artificial
<220> FEATURE:
<223> OTHER INFORMATION: shRNA SEQ. for Human c-met -continued

---

<400> SEQUENCE: 12
caaactagag ttctccttgg aattcaagag attccaagga gaactctagt ttttttttgg      60
aa                                                                     62

<210> SEQ ID NO 13
<211> LENGTH: 21
<212> TYPE: DNA
<213> ORGANISM: Artificial
<220> FEATURE:
<223> OTHER INFORMATION: Target sequence in Human c-met

<400> SEQUENCE: 13
aaactagagt tctccttgga a                                                21

<210> SEQ ID NO 14
<211> LENGTH: 69
<212> TYPE: DNA
<213> ORGANISM: Artificial
<220> FEATURE:
<223> OTHER INFORMATION: shRNA SEQ for Mouse c-met

<400> SEQUENCE: 14
ctccacgtga acgctactta tgtgaattca agagattcac ataagtagcg ttcacgtgga      60
tttttggaa                                                              69

<210> SEQ ID NO 15
<211> LENGTH: 25
<212> TYPE: DNA
<213> ORGANISM: Artificial
<220> FEATURE:
<223> OTHER INFORMATION: Target sequence in Mouse c-met

<400> SEQUENCE: 15
tccacgtgaa cgctacttat gtgaa                                            25

<210> SEQ ID NO 16
<211> LENGTH: 63
<212> TYPE: DNA
<213> ORGANISM: Artificial
<220> FEATURE:
<223> OTHER INFORMATION: CRISPR gRNA SEQ for Human c-met

<400> SEQUENCE: 16
aatttctact aagtgtagat aatttctact aagtgtagat cactccccat tgctcctctg      60
cac                                                                    63

<210> SEQ ID NO 17
<211> LENGTH: 23
<212> TYPE: DNA
<213> ORGANISM: Artificial
<220> FEATURE:
<223> OTHER INFORMATION: Target sequence in Human c-met

<400> SEQUENCE: 17
gtgcagagga gcaatgggga gtg                                              23

<210> SEQ ID NO 18
<211> LENGTH: 3684
<212> TYPE: DNA
<213> ORGANISM: Artificial
<220> FEATURE:
<223> OTHER INFORMATION: Lbcpf1 SEQ

```
<400> SEQUENCE: 18
atgagcaagc tggagaagtt tacaaactgc tactccctgt ctaagaccct gaggttcaag      60
gccatccctg tgggcaagac ccaggagaac atcgacaata agcggctgct ggtggaggac     120
gagaagagag ccgaggatta taagggcgtg aagaagctgc tggatcgcta ctatctgtct     180
tttatcaacg acgtgctgca cagcatcaag ctgaagaatc tgaacaatta catcagcctg     240
ttccggaaga aaaccagaac cgagaaggag aataaggagc tggagaacct ggagatcaat     300
ctgcggaagg agatcgccaa ggccttcaag ggcaacgagg ctacaagtc cctgtttaag     360 aaggatatca tcgagacaat cctgccagag ttcctggacg ataaggacga gatcgccctg     420
gtgaacagct tcaatggctt taccacagcc ttcaccggct tctttgataa cagagagaat     480 atgtttccg aggaggccaa gagcacatcc atcgccttca ggtgtatcaa cgagaatctg     540
acccgctaca tctctaatat ggacatcttc gagaaggtgg acgccatctt tgataagcac     600
gaggtgcagg agatcaagga gaagatcctg aacagcgact atgatgtgga ggatttcttt     660
gagggcgagt tctttaactt tgtgctgaca caggagggca tcgacgtgta taacgccatc     720
atcggcggct tcgtgaccga gagcggcgag aagatcaagg gcctgaacga gtacatcaac     780
ctgtataatc agaaaaccaa gcagaagctg cctaagttta agccactgta taagcaggtg     840
ctgagcgatc gggagtctct gagcttctac ggcgagggct atacatccga tgaggaggtg     900
ctggaggtgt ttagaaacac cctgaacaag aacagcgaga tcttcagctc catcaagaag     960
ctggagaagc tgttcaagaa ttttgacgag tactctagcg ccggcatctt tgtgaagaac    1020
ggccccgcca tcagcacaat ctccaaggat atcttcggcg agtggaacgt gatccgggac    1080
aagtggaatg ccgagtatga cgatatccac ctgaagaaga aggccgtggt gaccgagaag    1140
tacgaggacg atcggagaaa gtccttcaag aagatcggct ccttttctct ggagcagctg    1200
caggagtacg ccgacgccga tctgtctgtg gtggagaagc tgaaggagat catcatccag    1260
aaggtggatg agatctacaa ggtgtatggc tcctctgaga agctgttcga cgccgatttt    1320
gtgctggaga gagcctgaa gaagaacgac gccgtggtgg ccatcatgaa ggacctgctg    1380
gattctgtga gagcttcga gaattacatc aaggccttct ttggcgaggg caaggagaca    1440
aacagggacg agtccttcta tggcgatttt gtgctggcct acgacatcct gctgaaggtg    1500
gaccacatct acgatgccat ccgcaattat gtgacccaga gccctactc taaggataag    1560 ttcaagctgt attttcagaa ccctcagttc atgggcggct gggacaagga taaggagaca    1620
gactatcggg ccaccatcct gagatacggc tccaagtact atctggccat catggataag    1680
aagtacgcca gtgcctgca gaagatcgac aaggacgatg tgaacggcaa ttacgagaag    1740
atcaactata gctgctgcc cggccctaat aagatgctgc caaaggtgtt ctttttctaag    1800 aagtggatgg cctactataa ccccagcgag gacatccaga gatctacaa gaatggcaca    1860 ttcaagaagg cgatatgtt taacctgaat gactgtcaca gctgatcga cttctttaag    1920 gatagcatct cccggtatcc aaagtggtcc aatgcctacg atttcaactt ttctgagaca    1980
gagaagtata aggacatcgc cggcttttac agagaggtgg aggagcaggg ctataaggtg    2040
agcttcgagt ctgccagcaa gaaggaggtg ataagctgg tggaggaggg caagctgtat    2100
atgttccaga tctataacaa ggactttccc gataagtctc acggcacacc caatctgcac    2160
accatgtact tcaagctgct gtttgacgag aacaatcacg gacagatcag gctgagcgga    2220
ggagcagagc tgttcatgag gcgcgcctcc ctgaagaagg aggagctggt ggtgcaccca    2280
gccaactccc ctatcgccaa caagaatcca gataatccca agaaaaccac aaccctgtcc    2340
```

```
tacgacgtgt ataaggataa gaggttttct gaggaccagt acgagctgca catcccaatc      2400
gccatcaata agtgccccaa gaacatcttc aagatcaata cagaggtgcg cgtgctgctg      2460
aagcacgacg ataacccta tgtgatcggc atcgataggg gcgagcgcaa tctgctgtat      2520
atcgtggtgg tggacggcaa gggcaacatc gtggagcagt attccctgaa cgagatcatc      2580
aacaacttca acggcatcag gatcaagaca gattaccact ctctgctgga caagaaggag      2640
aaggagaggt tcgaggcccg ccagaactgg acctccatcg agaatatcaa ggagctgaag      2700
gccggctata tctctcaggt ggtgcacaag atctgcgagc tggtggagaa gtacgatgcc      2760
gtgatcgccc tggaggacct gaactctggc tttaagaata gccgcgtgaa ggtggagaag      2820
caggtgtatc agaagttcga gaagatgctg atcgataagc tgaactacat ggtggacaag      2880
aagtctaatc cttgtgcaac aggcggcgcc ctgaagggct atcagatcac caataagttc      2940
gagagcttta agtccatgtc tacccagaac ggcttcatct tttacatccc tgcctggctg      3000
acatccaaga tcgatccatc taccggcttt gtgaacctgc tgaaaaccaa gtataccagc      3060
atcgccgatt ccaagaagtt catcagctcc tttgacagga tcatgtacgt gcccgaggag      3120
gatctgttcg agtttgccct ggactataag aacttctctc gcacagacgc cgattacatc      3180
aagaagtgga agctgtactc ctacggcaac cggatcagaa tcttccggaa tcctaagaag      3240
aacaacgtgt tcgactggga ggaggtgtgc ctgaccagcg cctataagga gctgttcaac      3300
aagtacggca tcaattatca gcagggcgat atcagagccc tgctgtgcga gcagtccgac      3360
aaggccttct actctagctt tatggccctg atgagcctga tgctgcagat gcggaacagc      3420
atcacaggcc gcaccgacgt ggattttctg atcagccctg tgaagaactc cgacggcatc      3480
ttctacgata gccggaacta tgaggcccag gagaatgcca tcctgccaaa gaacgccgac      3540
gccaatggcg cctataacat cgccagaaag gtgctgtggg ccatcggcca gttcaagaag      3600
gccgaggacg agaagctgga taaggtgaag atcgccatct ctaacaagga gtggctggag      3660
tacgcccaga ccagcgtgaa gcac                                              3684
```

```
<210> SEQ ID NO 19
<211> LENGTH: 45
<212> TYPE: DNA
<213> ORGANISM: Artificial
<220> FEATURE:
<223> OTHER INFORMATION: linker sequence for IL-12

<400> SEQUENCE: 19
ggtggcggtg gctcgggcgg tggtgggtcg ggtggcggcg gatct                          45

<210> SEQ ID NO 20
<211> LENGTH: 582
<212> TYPE: DNA
<213> ORGANISM: Artificial
<220> FEATURE:
<223> OTHER INFORMATION: lRES sequence

<400> SEQUENCE: 20 gcccccccc ctaacgttac tggccgaagc cgcttggaat aaggccggtg tgcgtttgtc         60
tatatgttat tttccaccat attgccgtct tttggcaatg tgagggcccg gaaacctggc       120
cctgtcttct tgacgagcat cctagctag gggtctttcc cctctcgcca aaggaatgca       180
aggtctgttg aatgtcgtga aggaagcagt tcctctggaa gcttcttgaa gacaaacaac       240
gtctgtagcg accctttgca ggcagcggaa ccccccacct ggcgacaggt gcctctgcgg       300
```

-continued

```
ccaaaagcca cgtgtataag atacacctgc aaaggcggca caaccccagt gccacgttgt      360
gagttggata gttgtggaaa gagtcaaatg gctctcctca agcgtattca acaaggggct      420
gaaggatgcc cagaaggtac cccattgtat gggatctgat ctggggcctc ggtgcacatg      480
ctttacatgt gtttagtcga ggttaaaaaa acgtctaggc cccccgaacc acggggacgt      540
ggttttcctt tgaaaaacac gatgataata tggccacaac ca                        582
```

ANTI-TUMOR COMPOSITION

TECHNICAL FIELD

The present invention relates to a composition for anti-tumor or enhancing antitumor immunity comprising a recombinant adenovirus that co-expresses interleukin-12 (IL-12) and a nucleic acid molecule inhibiting an expression of a tyrosine kinase Met (C-met).

BACKGROUND ART

Tumor immunotherapy is a method of inducing an immune response against a tumor by enhancing the overall immune function of the body and treating tumors through the same. Research on tumor immunotherapy is actively being conducted. However, an immunosuppressive environment is almost always formed at the stage at which cancer is generated, so that, even if the body's immune system is actively working, it is difficult to easily remove the tumor. Tumor cells themselves express many abnormal antigens. These antigens elicit an eradication reaction through immune surveillance, allowing tumor cells to evade immune surveillance even if the body's immune system is active. In addition, it has been found that the phenomenon is mediated by various factors produced by tumor cells. It has been reported that tumor tissues can produce immunosuppressive molecules such as vascular endothelial growth factor (VEGF), tumor growth factor (TGF)-β and interleukin (IL)-10, and regulatory T cells penetrate the immune-suppressed tumor. Further, stimulation of the expression of an inhibitory receptor called PD-1 continuously increases by activated T cells, and in the case of cancer cells, PD-L1, which is a ligand specifically binding to PD-1, is expressed in a large amount to inactivate activated T cells to avoid immune responses, resulting in an immune suppression microenvironment and immune tolerance in tumors.

A recent study has proved that an inhibitor capable of inhibiting the immune checkpoint of PD-1, which is involved in suppressing T cell activity, induces a strong antitumor immune response. Consequently, overcoming immune surveillance avoidance is a major strategy for immunotherapy. Therefore, as a way to overcome these limitations, research into directly introducing a cytokine gene having an immune-promoting effect into cancer cells to generate and secrete cytokines from cancer cells, and thus, specifically eliminating cancer cells through induction of antitumor immune responses is actively underway. Among the immune-enhancing cytokine genes for which antitumor effects have been reported to date, interleukin-12 (IL-12) is one of the most effective and promising cytokines.

Interleukin-12 (IL-12), which is a heterodimeric protein containing 40 kDa and 35 kDa subunits linked by disulfide bonds, is secreted from antigen presenting cells (APCs) such as activated macrophages, monocytes, dendritic cells and activated B lymphocytes, and acts directly on T cells and NK cells that can effectively eliminate cancer cells to activate the T cells and NK cells and induce the secretion of IFN-γ, as well as enhance the killing ability of the T cells and NK cells against cancer cells. Local expression of IL-12 makes tumor cells sensitive to T-cell mediated cytotoxicity, resulting in inhibition of tumor growth and establishment of systemic immunity.

However, there is a difficulty in the clinical application of IL-12 because the administration of IL-12 can cause systemic cytokine-associated toxicity that limits the patient's acceptable dose. In addition, overall downregulation of the immune effect, increased IL-10 expression in the patient's serum, and IL-12 polarization from Th1 to Th2 immunity due to decreased IFN-γ and TNF-β expression occur. For this reason, IL-12 is sometimes repeatedly administered. These clinical results show the limitations of IL-12 as a single treatment for the treatment of cancer.

Recently, studies on growth factors and receptors thereof as biological indicators reflecting the degree of malignant cancer are underway. Thereamong, studies on C-met, which is a member of the tyrosine kinase receptor family, are being actively conducted. C-met acts as a receptor for hepatocyte growth factor/scatter factor (HGF/SF), and is overexpressed in various cancers. Most patients with C-met overexpression have a poor cancer treatment prognosis. The overexpression of C-met enhances mitogenesis and cellular motility due to the HGF/SF-Met signaling system, inhibits apoptosis, forms blood vessels, and induces invasion and migration into the extracellular matrix (ECM), i.e., causes an increase in cancer malignancy. Since rapid proliferation and migration of cancer cells induced by overexpression of C-met exceed the rate of removal of cancer cells in the immune system, it is difficult to eliminate the cancer cells through an immune response. Furthermore, since the center of the immune response in a tumor microenvironment is inclined severely toward inhibition as the size of the tumor increases, it is more difficult to control tumor cells using a single therapy, and the improved antitumor effect by antitumor immunotherapy cannot be achieved.

Therefore, the development of anticancer therapies without side effects depending on dosage, etc., while having better anticancer effects by increasing antitumor immunity remains a task to be solved in the art.

DISCLOSURE

Technical Problem

Therefore, the present invention has been made in view of the above problems, and the present inventors have tried to develop a treatment target capable of lowering the dosage while having excellent antitumor effect, and propose a method that can more effectively treat cancer by using a combination of treatment targeting IL-12 and C-met. The present inventors confirmed that it is possible to suppress tumors and overcome immune surveillance avoidance to obtain a synergistic effect in treating cancer, compared to the case of using each therapeutic target alone, by using adenovirus capable of inhibiting the overexpression of C-met while expressing interleukin-12 in the treatment of cancer, thus completing the present invention.

Throughout the present specification, a number of papers and patent documents are referenced and citations are indicated. The disclosed contents of the cited papers and patent documents are incorporated by reference in the present specification as a whole, so that the level of the technical field, to which the present invention belongs, and the contents of the present invention are more clearly described.

Technical Solution

In accordance with an aspect of the present invention, the above and other objects can be accomplished by the provision of a gene delivery system, comprising a gene encoding interleukin-12 (IL-12); and a gene expressing an oligonucleotide that is complementary to mRNA of C-met to inhibit expression of C-met.

In accordance with another aspect of the present invention, there is provided a pharmaceutical composition comprising a gene delivery system that comprises a nucleic acid sequence encoding interleukin-12 (IL-12); and a nucleic acid sequence expressing an oligonucleotide binding complementarily to C-met gene and inhibit expression of C-met.

The gene delivery system may be an adenovirus system, and the adenovirus system may be a recombinant adenovirus, or a recombinant adenoviral DNA.

The pharmaceutical composition may be an anticancer composition or a composition for enhancing antitumor immunity.

Advantageous Effects

An adenovirus system co-expressing interleukin-12 and a C-met expression-inhibiting nucleic acid molecule according to the present invention can restore immune functions in a tumor environment to remarkably enhance anticancer effects such as tumor remodeling and migration inhibition and tumor growth inhibition. Particularly, the adenovirus system can provide remarkable synergistic effects in the treatment of cancer due to co-expression of both the therapeutic genes.

DESCRIPTION OF DRAWINGS

FIG. 1 illustrates the structure of an adenovirus plasmid DNA constructed according to an embodiment of the present invention.

FIG. 2 illustrates that an adenovirus plasmid DNA constructed according to an embodiment of the present invention can express mouse interleukin-12 (mIL-12) or human interleukin-12 (hIL-12) in cells.

FIG. 3 illustrates that an adenovirus constructed according to an embodiment of the present invention increases the expression of interleukin-12 (IL-12) and inhibits the expression of C-met.

FIG. 4 illustrates anticancer adenovirus structures that co-express IL-12 and she-met constructed according to an embodiment of the present invention.

FIGS. 5a and 5b illustrate in vivo antitumor effects of an anticancer adenovirus co-expressing IL-12 and she-met according to an embodiment of the present invention in mouse-derived B16-F10 and CT26 cells, respectively.

FIG. 6 illustrates in vivo antitumor effects of an anticancer adenovirus pDNA/PPA complex co-expressing IL-12 and she-met according to an embodiment of the present invention in mouse-derived B16-F10 cells.

FIGS. 7a and 7b illustrate in vivo IL-12 expression (FIG. 7a) and in vivo C-met expression inhibition ability (FIG. 7b) of an anticancer adenovirus co-expressing IL-12 and she-met according to an embodiment of the present invention in human lung cancer cell line H1975.

FIGS. 8a and 8b illustrate cancer cell killing ability of anticancer adenoviruses expressing IL-12 and/or she-met according to embodiments of the present invention in human lung cancer cell line H1975 under a normal oxygen condition (8a) and low oxygen condition (8b).

FIGS. 9a, 9b, 9c and 9d illustrate HUVEC cell migration (9a and 9b) and invasion (9c and 9d) inhibition effects of anticancer adenoviruses expressing IL-12 and/or she-met according to embodiments of the present invention.

FIG. 10 illustrates tumor cell migration inhibition through Endothelial to Mesenchymal Transition (Endo-MT) inhibition in HUVEC cells by anticancer adenoviruses expressing IL-12 and/or she-met according to embodiments of the present invention.

FIG. 11 illustrates antitumor effects in a human xenograft tumor model (H1975) by anticancer adenoviruses expressing IL-12 and/or she-met according to embodiments of the present invention.

FIG. 12 schematically illustrates the structure of a gene delivery system that co-expresses IL-12; and a CRISPR/Cas system comprising a C-met-targeting guide RNA according to an embodiment of the present invention.

FIGS. 13a, 13b and 13c illustrate intercellular IL-12 expression effect (13a) and C-met inhibition effect (13b and 13c) by an anticancer virus co-expressing IL-12 and Lbcpf1-crMET according to an embodiment of the present invention.

FIG. 14 illustrates the antitumor effect in a human xenograft tumor model (H1975) of an anticancer virus co-expressing IL-12 and Lbcpf1-crMET according to an embodiment of the present invention.

MODES OF THE INVENTION

In accordance with an aspect of the present invention, the present invention provides a gene delivery system comprising a gene encoding interleukin-12 (IL-12); and a gene expressing an oligonucleotide that complementarily binds to the C-met gene to inhibit the expression of C-met.

In accordance with another aspect of the present invention, the present invention provides an anticancer composition that comprises a gene delivery system comprising a gene encoding interleukin-12 (IL-12); and a gene expressing an oligonucleotide that complementarily binds to the C-met gene to inhibit the expression of C-met; an anti-metastatic composition for cancer cells which comprises the gene delivery system; or a pharmaceutical composition for enhancing antitumor immunity which comprises the gene delivery system.

In accordance with still another aspect of the present invention, the present invention provides the use of a gene delivery system, which comprises a gene encoding interleukin-12 (IL-12); and a gene expressing an oligonucleotide that complementarily binds to the C-met gene to inhibit the expression of C-met, as an anticancer agent.

In accordance with yet another aspect of the present invention, the present invention provides a method of treating cancer, the method comprising administering a gene delivery system, which comprises a gene encoding interleukin-12 (IL-12); and a gene expressing an oligonucleotide that complementarily binds to the C-met gene to inhibit the expression of C-met, or a pharmaceutical composition comprising the gene delivery system to a subject.

In the present invention, the term "gene delivery system" refers to a vector system for delivering a gene into cells. In the present invention, unless otherwise specified, a gene delivery system, an adenovirus vector, an adenovirus system, or an adenovirus vector system has the same meaning. The adenovirus system of the present invention comprises both adenovirus and DNA of adenovirus (viral DNA). Preferably, the adenovirus system may be a recombinant adenovirus or a recombinant adenoviral DNA for anticancer or antitumor immunity enhancement.

The adenovirus system may include the genomic sequence of an adenovirus, so that an adenovirus is generated from an adenovirus or recombinant DNA delivered into a cell, thereby having an anticancer or antitumor immune effect. In the present invention, since the genes respectively expressing IL-12 and she-met may be inserted into the adenovirus genome and may be delivered to cells in the form of adenovirus itself or recombinant DNA thereof, an adenovirus comprises both a recombinant adenovirus and a recombinant adenoviral DNA throughout the specification of the present invention unless otherwise stated.

In accordance with a preferred embodiment of the present invention, the adenovirus system of the present invention may be an oncolytic adenovirus (oAd) capable of specifically proliferating only in a tumor and selectively killing tumor cells. The "oncolytic adenovirus" may be used interchangeably with terms such as anticancer virus, oAd, or tumor killing virus in the present specification. All of the oncolytic adenoviruses genetically modified through conventional techniques used in the art to which the present invention pertains are included in the adenovirus system of the present invention. For example, E1A and/or E1B may be removed from the adenovirus genome to proliferate only in cancer cells, thereby not proliferating in normal cells, or the target sequence of the viral protein may be changed to use a protease secreted from cancer cells, or a sequence expressing a ligand is inserted into a viral genome so as to express a receptor ligand to be bound to a receptor (e.g., EGFR) present in cancer cells.

In addition, to improve the killing ability of cancer cells, the TRAIL gene may be inserted into the tumor-selective oncolytic adenovirus of the present invention so that cell death occurs well, or the IFN gene may be applied to the tumor-selective oncolytic adenovirus to be inserted into cancer cells and effectively expressed therein so that an immune response occurs.

A recombinant adenovirus used in the present invention comprises a promoter operable in animal cells, preferably mammalian cells. Promoters suitable for the present invention include promoters derived from mammalian viruses and promoters derived from the genome of mammalian cells. A transgene inserted into the recombinant adenovirus is preferably inserted into an expression cassette of a promoter-trans gene poly A sequence. In this case, as the promoter, the gene expression control sequences of the present invention (HRE-TERT, HRE-E2F, HRE-TERT-E2F, HRE-E2F-TERT, HRE-E2F-5myc-TERT, and HRE may be included twice) or general promoters may be used.

General promoters bound to a transgene operate preferably in animal cells, more preferably mammalian cells, to control transcription of the transgenes. General promoters include a promoter derived from a mammalian virus and a promoter derived from the genome of a mammalian cell. Examples of general promoters include U6 promoter, H1 promoter, cytomegalovirus (CMV) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, tumor cell specific promoter (e.g., TERT promoter, PSA promoter, PSMA promoter, CEA promoter, E2F promoter and AFP promoter) and tissue specific promoter (e.g., albumin promoter), but the present disclosure is not limited thereto. It is preferred that the expression constructs for expressing a transgene comprises polyadenylated sequences bound to a downstream of the transgene. The polyadenylated sequences include bovine growth hormone terminator (Gimmi, E. R., et al., Nucleic Acids Res. 17: 6983-6998 (1989)), polyadenylated sequence derived from SV40 (Schek, N, et al., Mol. Cell Biol. 12:5386-5393(1992)), HIV-1 poly A (Klasens, B. I. F., et al., Nucleic Acids Res. 26:1870-1876(1998)), β-globin polyA (Gil, A., et al, Cell 49: 399-406(1987)), HSV TK polyA (Cole, C. N. and T. P. Stacy, Mol. Cell. Biol. 5:2104-2113(1985)) or polyomavirus polyA (Batt, D. B and G. G. Carmichael, Mol. Cell. Biol. 15:4783-4790(1995)), but the present disclosure is not limited thereto.

In the recombinant adenovirus used in the present invention, the IL-12 gene sequence and the sequence expressing RNA that inhibits C-met are operably linked to a promoter. In the present specification, the term "operably linked" refers to a functional linkage between a nucleic acid expression control sequence (e.g., a promoter, a signal sequence, or an array of transcriptional regulatory factor binding sites) and another nucleic acid sequence. Accordingly, the regulatory sequence controls the transcription and/or translation of the different nucleic acid sequences.

The recombinant adenovirus of the present invention may additionally include an antibiotic resistance gene and a reporter gene (e.g., green fluorescence protein (GFP), luciferase, and β-glucuronidase) as selectable markers. The antibiotic resistance gene comprises antibiotic resistance genes generally used in the art, and for example, may be a resistance gene against ampicillin, gentamicin, carbenicillin, chloramphenicol, streptomycin, kanamycin, geneticin, neomycin, or tetracycline, preferably a neomycin resistance gene. The selectable marker may be expressed by a separate promoter, an internal ribosome entry site (IRES), or an expression system linked by a 2A system, and IRES used in the present invention is a regulatory sequence found in RNAs of several kinds of viruses and cells (McBratney et. al. Current Opinion in Cell Biology 5:961 (1993)). In addition, "2A peptide" means a sequence encoding a cuttable small peptide (18-22 amino acids) that allows for efficient, concordant expression of discrete protein products within a single coding sequence. For example, the 2A peptide from a virus such as foot-and-mouth disease virus (F2A), equine Rhinitis A virus, porcine teschovirus-1 (P2A) or Thosea asigna virus (T2A), or any of the 2A peptides described in Szymczak-Workman, A. et al. "Design and Construction of 2A Peptide-Linked Multicistronic Vectors" may be used.

The present invention comprises both a gene encoding interleukin-12 (IL-12); and a gene expressing an oligonucleotide that is complementary to mRNA of C-met (tyrosine kinase Met) and inhibits the expression of C-met and provides a synergistic effect in enhancing anticancer and antitumor immunity by co-expressing both the genes. In addition, the present technology is significant in that it is possible to provide an excellent therapeutic effect despite the administration of IL-12 in a small amount, and to solve the problem of side effects caused by conventional cytokine administration.

In the present specification, the term "interleukin-12 (IL-12)" refers to a heterodimeric cytokine formed by a 40 kDa subunit (p40 subunit) and a 35 kDa subunit (p35 subunit) bound by a disulfide bond. IL-12 is produced by antigen-presenting cells such as macrophages and binds to receptors on cell surfaces of activated T cells, B cells and NK cells. IL-12 promotes proliferation of T cells and NK cells; enhances the cytotoxic effect of T cells, NK cells and macrophages; induces the production of IFN-γ, TNF-α and GM-CSF; and induces the activation of Th1 cells. In addition, IL-12 is known as an important co-stimulator of Th1 clone proliferation, and is known to increase the production of IgG2a antibodies in serum. In the present invention, the term "p35 subunit" and "p40 subunit" include not only the subunits exemplified in the examples, but also all analogs of subunits capable of performing unique functions of each subunit.

The adenovirus system of the present invention contains a gene encoding IL-12 in an expressible form, and secretes IL-12 after infection with tumor cells to induce a strong antitumor immune response.

The adenovirus system of the present invention may include IL-12A (p35) gene and IL-12B (p40) gene expressing IL-12A (p35) and IL-12B (p40), as subunits, so as to efficiently express IL-12. In addition, a linker sequence may be additionally included between the IL-12A (p35) gene sequence and the IL-12B (p40) gene sequence to serve to link the two subunits, or an internal ribosome entry site (IRES) sequence may be further included used to increase the efficiency of protein expression.

The linker means any sequence that can be included between two genes, and in the present invention, the linker means a sequence that can be included between the IL-12A (p35) gene and the IL-12B (p40) gene. The linker comprises all conventional linker sequences or randomly designed sequences known to be inserted between genes, and any linkers may be included in the present invention as long as they do not adversely affect the expression of IL-12 or impair the functionality of IL-12. For example, the liker may be the sequence of SEQ ID NO: 19, but the present invention is not limited thereto.

The amino acid sequence of "IL-12A subunit (p35 subunit)" that can be used in the present invention may be those described in GenBank accession number AAD56385 (when it is desired to express the amino acid sequence of mouse p35, GenBank Accession No. AAA39292). In addition, IL-12A (p35) gene, as a sequence encoding the IL-12A subunit, may be a nucleotide sequence corresponding to a coding sequence (CDS) among sequences described in Gen-Bank Accession No. AF180562 (when it is desired to use a mouse sequence, refer to the CDS sequence among the sequences described in M86672). In addition, IL-12A (p35) gene may have the sequence of SEQ ID NO: 1 or SEQ ID NO: 4 used in an embodiment of the present invention (in the case of a mouse, the sequence of SEQ ID NO: 7).

The amino acid sequence of "IL-12B subunit (p40 subunit)" that can be used in the present invention may be those described in GenBank accession number AAD56386 (when it is desired to express the amino acid sequence of mouse p40, GenBank Accession No. AAA39296). In addition, IL-12B (p40) gene, as a sequence encoding the IL-12B subunit, may be a nucleotide sequence corresponding to a coding sequence (CDS) among sequences described in Gen-Bank Accession No. AF180563 (when it is desired to use a mouse sequence, refer to the CDS sequence among the sequences described in M86671). In addition, it may be the sequence of SEQ ID NO: 2 or SEQ ID NO: 5 used in an embodiment of the present invention (in the case of a mouse, the sequence of SEQ ID NO: 8).

In an embodiment of the present invention, it was confirmed that IL-12 can be expressed in tumor cells by using the IL-12 gene of SEQ ID NO: 3 or SEQ ID NO: 6 (SEQ ID NO: 9 in the case of a mouse), particularly when expressed simultaneously with RNA for C-met, the expression level of 12 was significantly increased.

In the present specification, the term "'C-met" is one of the tyrosine kinase receptor family C-met acts as a receptor for hepatocyte growth factor/scatter factor (HGF/SF) and is overexpressed in various cancers. Most patients with c-met overexpression have poor cancer treatment prognosis. The C-met gene of the present invention may be a nucleotide sequence corresponding to a coding sequence (CDS) among the mRNA sequences disclosed in GenBank Accession No. gi: 4557746 (when it is desired to use a mouse sequence, refer to a CDS sequence among the sequences described in Accession No. gi: 146198695).

The overexpression of C-met increases mitogenesis and cell motility due to the HGF/SF-Met signaling system, and induces invasion and migration into the extracellular matrix, thereby increasing the malignancy of cancer. Therefore, in the treatment of cancer, the inhibition of C-met expression is a very important issue. The present invention inhibits the expression of C-met using an oligonucleotide that is complementary to the mRNA of C-met and inhibits the expression of C-met, particularly confirmed that the inhibition of C-met expression is remarkably enhanced, compared a group in which the expression of C-met is only inhibited, when the oligonucleotide is co-expressed with IL-12.

In an embodiment, mRNA of C-met, which is an inhibitory target, in the present invention may be the sequence shown in SEQ ID NO: 10 (in the case of a mouse, SEQ ID NO: 11).

An oligonucleotide that binds to the C-met gene to inhibit the expression of C-met may be one or more selected from the group consisting of shRNA, miRNA, siRNA, antisense oligonucleotides, ribozymes, DNAzyme, triplex forming oligonucleotides (TFOs), peptide nucleic acids (PNA), and guide RNA for CRISPR.

The oligonucleotide sequence inhibiting the expression of C-met may include a sequence identical or complementary to a part of the C-met mRNA sequence of SEQ ID NO: 10, preferably comprises a sequence identical or complementary to the sequence of 4 or more consecutive nucleotides in the sequence of SEQ ID NO: 10.

In an embodiment of the present invention, it was confirmed that the expression of C-met in tumor cells can be efficiently inhibited by using shRNA, which comprises a sequence complementary to the mRNA of C-met and is capable of inhibiting the expression of C-met, as the oligonucleotide.

In the present invention, "shRNA" (small hairpin RNA or short hairpin RNA), which is an artificial RNA molecule having a hairpin structure, is used to suppress the expression of a target gene through RNA interference. shRNA is primarily transported into cells via plasmid, bacterial or viral vectors. The shRNA has the advantage of relatively low rate of degradation and turnover.

In an embodiment of the present invention, it was confirmed that the expression of C-met is efficiently inhibited by the viral system of the present invention that uses shRNA, "Hshc-met (targeting the sequence of SEQ ID NO: 13)" or "shc-met (targeting the sequence of SEQ ID NO: 15)," encoded by the gene of SEQ ID NO: 12 (human) or SEQ ID NO: 14 (mouse) as shRNA for inhibiting the expression of C-met.

An oligonucleotide that binds to the C-met gene to inhibit the expression of C-met may be guide RNA for CRISPR. When the gene delivery system of the present invention expresses a CRISPR-CAS system, a sequence expressing Cas protein may be further included.

In the present invention, the "CRISPR-CAS system" refers to a technology of recognizing a specific nucleotide sequence present on a target DNA and cuts the DNA with a restriction enzyme to correct a gene. In the present invention, the CRISPR-CAS system is characterized in that when a sequence expressing a guide RNA for the target gene C-met is inserted into an adenovirus system, and the expressed guide RNA hybridizes to the target C-met, the target site is cleaved using Cas protein to inhibit the expression of C-met.

Unless otherwise stated, a method of constructing the CRISPR-CAS system, the type of restriction enzyme protein to be used in the CRISPR-CAS system, etc. may be used using techniques commonly used in the technical field of the present invention.

The Cas protein used in the present invention may be a Cas9 or Cas12 protein. Cas9 or Cas12 (also referred to as Cas12a or Cpf1) protein used in the present invention may be used without limitation so long as it is a Cas protein commonly used to implement the CRISPR/Cas system in the technical field of the present invention. In addition, examples of specific types of the Cas9 or Cas12 protein are as shown in Table 1 below, but are not limited thereto. The references listed in Table 1 are included in the specification of the present invention as a whole.

10 inhibited through the CRISPR-CAS system of crRNA-LbCpf1 by using the 55th to 77th nucleotides in the human C-met mRNA of SEQ ID NO: 10 as the target sequence (SEQ ID NO: 17) and by using an adenovirus system comprising the gene of SEQ ID NO: 16 expressing the guide RNA for CRISPR which can be complementarily hybridized to the target sequence; and the gene of SEQ ID NO: 18 expressing Lbcpf1.

In an embodiment of the present invention, the CRISPR-CAS system was expressed using a recombinant adenovirus vector containing a gene sequence expressing LbCpf1, as shown in FIG. 13.

In the present invention, the term "complementary" is meant to encompass not only 100% complementary, but also incomplete complementarity sufficient to suppress the expression of the C-met gene through an RNA interference mechanism, and preferably 90% complementarity, more preferably 98% complementarity, most preferably 100%

TABLE 1

| Type | PAM | Size | Cleaved shape | Origin |
|---|---|---|---|---|
| SpCas9 | 5'-NGG | 4.2 kb | Blunt | *Streptococcus pyogenes* |
| SaCas9 | 5'-NNGRRT | 3.15 Kb | Blunt | *Staphylococcus aureus* |
| CjCas9 | 5'-NNNNRYAC | 2.95 Kb | Blunt | — |
| Cas12a (type-V Cpf1) | 5'-TTTV | 3.9 kb | Staggered | *Lachnospiraceae bacterium* (LbCpf1); *Acidaminococcus* sp. (AsCpf1); *Francisella novicida* (FnCpf1); *Moraxella bovoculi* 237 (MbCpf1) |

R = purine, Y = pyrimidine.
V = Not U/T (A or C or G) see: *Christine* et al., *Viral Delivery Systems for CRISPR*, Viruses 2019, 11, 28

Cpf1 is a type of CRISPR/Cas system and is classified as Class 2 Type 5 CRISPR/Cas system. Cpf1 works as a single subunit effector module like Cas9, but is slightly different from Cas9 in terms of functionality, so that, while Cas9 requires tracrRNA to cut a gene, Cpf1 does not require tracrRNA. In the case of Cas9, a gene in a region with a protospacer-adjacent motif (PAM) containing a lot of guanine is cut off, whereas Cpf1 can efficiently cut a region having a lot of thymine. In addition, Cpf1 has a characteristic of generating a 4 to 5 nucleotide overhang when cutting a gene. Due to these various features and structural differences, Cpf1 exhibits higher accuracy even though the operating efficiency thereof is slightly lower than in Cas9.

A promoter for expression of the CRISPR-CAS system of the present invention may be any promoter, without limitation, as long as it is used in the CRISPR/Cas system in the technical field to which the present invention pertains. For example, an RNA polymerase III promoter which pertains to a type III class, or a U6 promoter may be used. In this case, since the commonly used U6 promoter requires guanosine nucleotides to initiate transcription, the use of the U6 promoter may further limit a genomic targeting site to GN$_{19}$NGG (Mali et al. (2013) Science 339:823-826; Ding et al. (2013) Cell Stem Cell 12:393-394). T7, T3 or SP6 promoter may also be used in the vector system of the present invention (Adhya et al. (1981) Proc. Natl. Acad. Sci. U.S.A. 78:147-151; Melton et al. (1984) Nucleic Acids Res. 12:7035-7056; Pleiss et al. (1998) RNA 4:1313-1317).

In an embodiment of the present invention, it was confirmed that the expression of C-met can be efficiently complementarity. In the present specification, when expressing 100% complementarity, it is described as "completely complementary".

In accordance with an embodiment of the present invention, the shRNA sequence included in the adenovirus of the present invention comprises a sequence that is complementary to some of the sequences of SEQ ID NO: 10, preferably a sequence that is complementary to the sequence of the 1987th nucleotide to the 2007th nucleotide of the C-met mRNA sequence of SEQ ID NO: 10.

In accordance with a specific embodiment of the present invention, shRNA, as an oligonucleotide capable of inhibiting the expression of C-met, may be encoded by the gene of SEQ ID NO: 12 or SEQ ID NO: 16 (in the case of a mouse, the gene of SEQ ID NO: 14).

"Gene or gene sequence" used in the present invention is interpreted as comprising a gene sequence showing substantial identity or substantial similarity to each sequence of the sequence numbers presented in the present invention. Substantial identity, when the sequence of the present invention and any other sequence are aligned to correspond to each other as much as possible, and when the aligned sequence is analyzed using an algorithm commonly used in the art, refers to a sequence that exhibits homology of more than 70%, preferably 80% homology, more preferably 90% homology, and most preferably 95% homology. Substantial similarity generally refers to a case in which changes in the sequence of IL-12 genes, such as deletion or insertion of one or more bases, do not affect the object of the present invention to minimize homologous recombination with the recombinant vector system. Accordingly, the IL-12 gene sequence of the present invention is not limited to the exemplified sequence lists, and it is construed as being included in the scope of the present invention so long as it does not substantially affect the activity of a desired final product of the present invention.

The adenovirus system of the present invention can achieve the treatment of cancer by using the genomic backbone of the adenovirus. Adenovirus is widely used as a gene delivery system due to a medium genome size thereof, ease of manipulation, high titer, a wide range of target cells, and excellent infectivity. Both ends of the genome contain 100 to 200 bp of an inverted terminal receptor (ITP), which is an essential component for DNA replication and packaging. The E1 region of the genome (E1A and E1B) encodes proteins that regulate transcription and transcription of host cell genes. The E2 region (E2A and E2B) encodes a protein involved in virus DNA replication. Since only a small portion of the adenovirus genome is known to be required in cis (Tooza, J. Molecular biology of DNA Tumor viruses, 2nd ed. Cold Spring Harbor Laboratory, Cold Spring Harbor, NY (1981)), adenoviruses have the ability to carry foreign DNA molecules.

In the genome of the adenovirus system of the present invention, the E1 and E3 regions may be deleted. Particularly, the adenovirus system of the present invention may include an E1A gene and an inactivated E1B 19 gene, an inactivated E1B 55 gene, or an inactivated E1B 19 gene and E1B 55 gene.

The term "inactivation" used in relation to a gene in the present specification means that the transcription and/or translation of the gene is not performed normally, and the function of the normal protein encoded by the gene does not appear. For example, in the case of the inactivated E1B 19 gene, an active E1B 19 kDa protein cannot be produced due to mutation (substitution, addition, partial deletion or total deletion) of E1B 19 gene. When E1B 19 is deleted, cell apoptosis can be increased, and when E1B 55 gene is deleted, the specificity of tumor cells is exhibited (see Patent Application No. 2002-23760). In the present specification, the term "deletion" used in relation to a gene or a sequence has a meaning comprising not only complete deletion of a corresponding sequence, but also partial deletion thereof.

The recombinant adenovirus of the present invention may have a mutation wherein the 45th Glu residue of a nucleotide sequence encoding an Rb binding site located in the E1A gene sequence is substituted with Gly, and a mutation wherein the 121-127th amino acid sequence thereof is entirely substituted with Gly.

In accordance with an embodiment of the present invention, the recombinant adenovirus may include the E1A site and E1B 19 kDa and E3 site (ΔE3) therein may be deleted. A recombinant adenovirus comprising E1A gene has a replicable property. The IL-12 gene and the C-met expression inhibition oligonucleotide may be inserted into the deleted E1 and E3 sites of adenovirus, respectively.

The adenovirus system of the present invention may further include a biocompatible polymer to increase the intracellular delivery ability of the adenovirus or viral DNA thereof, or to increase the remaining time, etc. by being delivered into cells. Particularly, the biocompatible polymer may be included, in a form of being combined with adenovirus or adenovirus plasmid DNA, in the system of the present invention.

The biocompatible polymer may be any one so long as it can be used in a vector system for gene delivery in the technical field of the present invention.

For example, the biocompatible polymer of the present invention may be a pH-sensitive and bioreducing polymer comprising (a) an escapable portion from immune reaction, (b) a chargeable portion, and (c) a bioreducible portion comprising a disulfide bond.

The escapable portion (a) from immune reaction functions to allow a virus, to which a polymer binds, to avoid immune responses in vivo (comprising cellular and systemic immunity reactions). A material that may be used in the escapable portion from immune reaction is particularly a polymer capable of escaping from an immune response in vivo (comprising cellular and systemic immunity reactions), more particularly PEG (polyethylene glycol), polyalkylene oxide (e.g., polyoxyethylene, polyoxypropylene or a copolymer thereof (a polyethylene oxide-polypropylene oxide-polyethylene oxide copolymer)), polyphenylene oxide, a copolymer of PEG and polyalkylene oxide, poly(methoxyethyl methacrylate), poly(methacryloyl phosphatidylcholine), perfluorinated polyether, dextran or polyvinylpyrrolidone, more particularly, PEG, polyalkylene oxide or a copolymer of PEG and polyalkylene oxide, even more particularly PEG.

The chargeable portion (b) may impart a positive charge to the polymer at in vivo pH, specifically near a neutral pH to be bound by interaction with a surface or DNA of a negatively charged virus. Alternatively, the chargeable portion (b) may impart negative charge to the polymer, as opposed to the above, depending on the chargeability of a viral surface or DNA. Accordingly, the chargeable portion (b) comprises a material that imparts a positive or negative charge to the polymer. For example, when a negative charge is imparted, a carboxylate group may be used in the chargeable portion (b), whereas, when a positive charge is imparted, a monomer having a tertiary amine group or an amino group may be used in the chargeable portion (b).

The bioreducible portion (c) comprising a disulfide bond may be included in the present invention without being limited to the type of monomer so long as it comprises a disulfide bond. The bioreducible portion (c) is reduced in an acidic environment in vivo so that a disulfide bond is converted to a sulfhydryl group, and thus the polymer structure is broken, and eventually a naked virus or DNA bound to a polymer-virus complex or a polymer-DNA complex is released.

In another embodiment, the biocompatible polymer of the present invention may include all of a polymer, a nanomaterial, a dendrimer, and a hydrogel. The biocompatible polymer is preferably selected from the group consisting of PEI-Arg-mPEG-S-S-mPEG-Arg-PEI (PAPS), mPEG-PEI-g-Arg-S-S-Arg-g-PEI-mPEG (PPSA), PICION (pegylated and iron oxide nanoparticles-crosslinked catechol-grafted poly L lysine (PLL)), an arginine-grafted biodegradable polymer (ABP), a pegylated and PTX-conjugated polymeric micelle (APP), mPEG-b-Pip-CBA (PPCBA), PPCBA-PEI-Arginine (PPA), polyethyleneglycol (PEG), poly-lactide (PLA), polyglycolide (PGA), poly-lactide-co-glycolide (PLGA), poly-ε-caprolactone (PCL), polyethylenimine (PEI), hyaluronic acid (HA), gelatin, chitosan, and serum albumin.

The PAPS polymer is PEI-Arg-mPEG-S-S-mPEG-Arg-PEI and may have the structure of the following Structural Formula 1:

[Structural Formula 1]

In Structural Formula 1, x and y may each independently be an integer of 1 to 500.

The PPSA polymer is mPEG-PEI-g-Arg-S-S-Arg-g-PEI-mPEG and may have the structure of the following Structural Formula 2:

[Structural Formula 2]

In Structural Formula 2, n and m may each independently be an integer of 1 to 500.

The PICION is pegylated and iron oxide nanoparticles-crosslinked catechol-grafted poly L lysine (PLL), and may have a structure wherein the catechol-grafted poly L lysine of the following Structural Formula 3 is crosslinked with iron oxide particles, and mPEG is modified on a surface thereof:

[Structural Formula 3]

In Structural Formula 3, n may be an integer of 1 to 500.

The ABP polymer is an arginine-grafted biodegradable polymer (arginine grafted bio-reducible polymer), and may have the structure of the following Structural Formula 4:

[Structural Formula 4]

In Structural Formula 4, n may be an integer of 1 to 500.

The APP is a pegylated and PTX-conjugated polymeric micelles (PEGylated and PTX-conjugated polymeric micelle, and may have the structure of the following Structural Formula 5:

[Structural Formula 5]

-continued

In Structural Formula 5, n and m may each independently be an integer of 1 to 500.

The PPCBA polymer is mPEG-b-Pip-CBA, belongs to a pH-sensitive and biodegradable polymer, and may have the structure of the following Structural Formula 6:

[Structural Formula 6]

In Structural Formula 6, n and m may each independently be an integer of 1 to 500.

The PPA is PPCBA-PEI-Arginine, belongs to a pH-sensitive and biodegradable polymer, and may be a polymer in which PEI and arginine are further bound to PPCBA. The PPA may have the structure of the following Structural Formula 7:

[Structural Formula 7]

23

In Structural Formula 7, a, b and c may each independently be an integer of 1 to 500. For example, a may be 100 to 200, b may be 1 to 10, and c may be 1 to 5, or a may be 113, b may be 6, and c may be 1, but the present invention is not limited thereto.

Polyethylenimine (PEI) may include all linear or branched polyethylenimines to which the monomer of Structural Formula 8 is bound.

[Structural Formula 8]

In Structural Formula 8, n may be an integer of 1 to 500.

The branched polyethylenimine may also include a dendrimer wherein chains of molecules are regularly spread, in a three-dimensional manner, outward from the center according to a certain rule, in addition to general branched polyethylenimines

24

[Structural Formula 9]

Structural Formula 9 represents an example of branched polyethylenimine Here, n may be an integer of 1 to 500.

The biodegradable polymer of the present invention comprises a dendrimer polymer that is an example of the polymer of Structural Formula 8 comprising ethyleneamine as a monomer. For example, a dendrimer-type branched polyethylenimine may be the polymer of Structural Formula 10 or 11, but the present disclosure is not limited thereto. The polymer of Structural Formula 11 is a poly(amidoamine) polymer and may also be referred to as PAMAM.

[Structural Formula 10]

-continued

[Structural Formula 11]

The biocompatible polymer binds with the recombinant adenovirus or viral DNA of the present invention to increase the efficiency of inflow into cells, increases stability in an individual, and improves delivery efficiency of a virus or viral DNA to a target site by lowering immunogenicity, thereby significantly increasing the cancer treatment effect due to the adenovirus or viral DNA of the present invention.

The biocompatible polymer and the adenovirus system may be connected by electrostatic interaction, ionic interaction or chemical bonding.

In accordance with another aspect of the present invention, the present invention provides a pharmaceutical composition that comprises a gene delivery system comprising a nucleic acid sequence encoding interleukin-12 (IL-12); and a nucleic acid sequence expressing an oligonucleotide that binds complementarily to the C-met gene and inhibits the expression of C-met. The composition may be an anticancer composition, an anti-metastatic composition for cancer cells, or a composition for enhancing antitumor immunity.

The composition may include the adenovirus system of the present invention in a therapeutically effective amount. In addition, the composition may further include a pharmaceutically acceptable carrier.

The anticancer composition serves to inhibit the survival, proliferation, and/or migration of tumor cells to inhibit the proliferation of cancer cells or to induce or promote the death of cancer cells. The recombinant adenovirus system of the present invention or a composition comprising the same can efficiently induce the death of cancer cells and inhibit migration thereof.

The anti-metastatic composition for cancer cells has an effect of inhibiting migration of cancer cells through migration. For example, it can be confirmed that the anti-metastatic composition inhibits EMT in cancer cells, thereby inhibiting migration thereof. The anti-metastatic composition of the present invention may have both an anticancer effect through killing of cancer cells and an effect of inhibiting migration of cancer cells.

The composition for enhancing antitumor immunity is capable of treating cancer by overcoming immune surveillance avoidance of a tumor using an immunosuppressive molecule produced in tumor tissue, and may be included in an anticancer composition. Particularly, the antitumor immunity composition serves to normalize the imbalance of immune cells in tumor tissues and induce differentiation of T helper cells by IL-12, thereby activating the cytotoxicity of cytotoxic T lymphocytes and natural killer cells, resulting in enhanced anticancer immunity.

The pharmaceutical composition of the present invention expresses IL-12 to enhance anticancer immunity in a cancer subject. In addition, the expression of C-met is inhibited through shRNA against C-met, thereby further amplifying the function of IL-12. In an embodiment of the present invention, it was confirmed that, even in a mouse model injected with human-derived cancer cells, remarkable anticancer effects and tumor migration effects appeared when the IL-12 and she-met co-expressing adenovirus of the present invention was injected.

In addition, the composition may be a composition for adjuvant treatment to enhance the therapeutic effect of standard therapy, or a composition for adjuvant treatment to improve or enhance the effect of standard therapeutic agents comprising other anticancer agents, immune checkpoint inhibitors, and immunotherapy agents, etc.

The anticancer composition of the present invention uses the recombinant adenovirus included in the aforementioned composition for antitumor immunity enhancement. Accordingly, descriptions of the same contents are omitted to avoid excessive complexity of the present specification.

In accordance with an embodiment of the present invention, the cancer may be selected from the group consisting of gastric cancer, lung cancer, non-small cell lung cancer, breast cancer, ovarian cancer, liver cancer, bronchial cancer, nasopharyngeal cancer, laryngeal cancer, pancreatic cancer, bladder cancer, colorectal cancer, colon cancer, cervical cancer, bone cancer, non-small cell bone cancer, blood cancer, skin cancer (melanoma etc.), head or neck cancer, uterine cancer, rectal cancer, anal cancer, colon cancer, fallopian tube cancer, endometrial cancer, vaginal cancer, vulvar cancer, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, kidney or ureter cancer, renal cell carcinoma, renal pelvic carcinoma, polyploid carcinoma, salivary gland cancer, sarcoma cancer, pseudomyxoma, hepatoblastoma, testicular cancer, glioblastoma, cleft lip cancer, ovarian germ cell tumor, basal cell carcinoma, multiple myeloma, gallbladder cancer, choroidal melanoma, ampulla of vater cancer, peritoneal cancer, adrenal cancer, tongue cancer, small cell cancer, pediatric lymphoma, nerve blastoma, duodenal cancer, ureteral cancer, astrocytoma, meningioma, renal carcinoma, vulvar cancer, thymus cancer, central nervous system (CNS) tumor, primary central nervous system lymphoma, spinal cord tumor, brain stem glioma, and pituitary adenoma, but the present invention is not limited thereto.

All of the aforementioned compositions of the present invention include a pharmaceutically acceptable carrier. A pharmaceutically acceptable carrier used in the present invention is one commonly used in formulation and comprises lactose, dextrose, sucrose, sorbitol, mannitol, starch, gum acacia, calcium phosphate, alginate, gelatin, calcium silicate, fine crystalline cellulose, polyvinylpyrrolidone, cellulose, water, syrup, methyl cellulose, methylhydroxybenzoate, propylhydroxybenzoate, talc, magnesium stearate, mineral oil, etc., but the present disclosure is not limited thereto. The pharmaceutical composition of the present invention may further include a lubricant, a wetting agent, a sweetening agent, a flavoring agent, an emulsifying agent, a suspending agent, a preservative, etc. in addition to the above components. Suitable pharmaceutically acceptable carriers and formulations are described in detail in Remington's Pharmaceutical Sciences (19th ed., 1995).

The composition of the present invention may be administered orally or parenterally. Parenteral administration may be intratumoral injection, intravenous injection, intradermal injection, subcutaneous injection, intramuscular injection, intraperitoneal injection, intrathecal injection, intracardiac injection, intrathoracic injection, intraarterial injection, intraosseous injection, intraarticular injection, transdermal administration, etc., preferably parenteral administration.

In addition, the composition may be for topical or systemic administration.

In accordance with an embodiment of the present invention, the antitumor immunity enhancement composition of the present invention is preferably administered directly intratumorally, thereby having an antitumor immunity enhancement effect.

A suitable dosage of the composition of the present invention may be varied depending upon factors such as a formulation method, an administration manner, a patient's age, weight, sex, pathological condition, and diet, an administration time, an administration route, an excretion rate, and response sensitivity. A daily dosage of the pharmaceutical composition of the present invention is, for example, 0.2 to 1,000 mg/kg. However, the actual dosage of an active ingredient can be determined in consideration of various related factors such as the amount of target tissue cells to be differentiated and proliferated, the route of administration, and a patient's weight, age, and sex. Accordingly, the dosage may be provided in any form without limiting the scope of the present invention.

In accordance with still another aspect of the present invention, the present invention provides the use of a gene delivery system, which comprises a gene encoding interleukin-12 (IL-12); and a gene expressing an oligonucleotide that complementarily binds to C-met gene to inhibit the expression of C-met, as an anticancer agent. The gene delivery system of the present invention co-expresses IL-12 and C-met-inhibiting RNA, thereby inhibiting tumor migration while further improving the antitumor immune effect of IL-12. The use of the gene delivery system of the present invention as an anticancer agent applies mutatis mutandis to the above description of the gene delivery system or pharmaceutical composition so as to avoid overlapping descriptions.

In accordance with yet another aspect of the present invention, the present invention provides a method of treating cancer, the method comprising administering a gene delivery system, which comprises a gene encoding interleukin-12 (IL-12); and a gene expressing an oligonucleotide that complementarily binds to C-met gene to inhibit the expression of C-met, or a pharmaceutical composition comprising the gene delivery system to a subject.

The gene delivery system of the present invention co-expresses IL-12 and C-met-inhibiting RNA, thereby inhibiting tumor migration while further improving the antitumor immune effect due to IL-12, resulting in a synergistic effect in cancer treatment. A method of treating with the gene delivery system of the present invention as an anticancer agent applies mutatis mutandis to the above description of the gene delivery system or pharmaceutical composition so as to avoid overlapping descriptions.

Hereinafter, the present invention will be described in more detail with reference to the following Examples. It will be apparent to those skilled in the art that the Examples are merely for concretely explaining the invention and therefore, there is no intent to limit the invention to the Examples.

EXAMPLES

Preparation of Experiment and Construction of Recombinant Vector

Preparation Example 1. Cell Obtainment and Culture

As a cell culture medium, Dulbecco's modified Eagle's Medium (DMEM; Gibco BRL, Grand Island, NY), Roswell Park Memorial Institute medium (RPMI; Gibco BRL), or Minimal Essential Medium (MEM; Gibco BRL) which contained 10% fetal bovine serum (FBS; Gibco BRL), L-glutamine (2 mmol/L), penicillin (100 IU/mL), and streptomycin (50 mg/mL) was used. HEK293 (expressing the adenovirus E1 site, human embryonic kidney cell line), H1975 (human non-small lung cancer cell line), and HaK (hamster kidney cancer cell line) were purchased from American Type Culture Collection, Manassas (ATCC, VA).

HaP-T1 (hamster pancreatic carcinoma cell line) was provided by Dr. Masato Abei (University of Tsukuba, Ibaraki, Japan). All cell lines were cultured under a humid environment of 37° C. and 5% $CO_2$, and were subjected to a mycoplasma negative test using Hoeschst dye, cell culture and PCR. E. coli (Escherichia coli) was cultured at 37° C. in Luria Bertani medium.

Manufacturing Example 1. Construction of Oncolytic Adenovirus System Expressing IL-12 and/or shc-met

Manufacturing Example 1-1. Construction of pDNA Expressing Human-Derived IL-12 and shc-met To investigate antitumor effects and antitumor immune response using an Ad vector, two oncolytic adenovirus plasmid DNAs (referred to as Ad pDNA or oAd pDNA) recombined based on mT-Rd19-RGD so as to express an antitumor immune gene, human interleukin-12 (hIL-12), and/or a short hairpin RNA (hereinafter referred to as "shc-met") complementarily binding to C-met to inhibit the expression of C-met playing an important role in cancer cell growth and differentiation were constructed (FIG. 1): (mT-Rd19-RGD and mT-Rd19-RGD/hIL-12/shc-met).

TABLE 2

|  | oAd pDNA structure | Remark |
| --- | --- | --- |
| Example 1 | mT-Rd19-RGD/hIL-12/shc-met (Pac I site 2) | hIL-12 and shc-met co-expressed, two Pac I sites |
| Example 2 | mT-Rd19-RGD/hIL-12/shc-met (Pac I site 1) | hIL-12 and shc-met co-expressed, one Pac I site |

Manufacturing Examples 1 to 2. Construction of Polymer-Viral DNA Complex Expressing Mouse-Derived IL-12 and Shc-Met In addition, a gene expressing mouse-derived IL-12 p35 (SEQ ID NO: 7) and IL-12 p40 (SEQ ID NO: 8) was inserted based on HE5cT-Rd19-RGD. In addition, a shRNA was designed using 4398th to 4422th nucleotides of the mouse C-met gene of SEQ ID NO: 11 as target sequences (SEQ ID NO: 15). HE5cT-Rd19-RGD/scIL-12/shc-met plasmid DNA, into which the nucleotide sequence of SEQ ID NO: 14 was inserted, complementarily binding to the C-MET gene and expressing shc-met that was capable of inhibiting the expression of the C-MET gene was constructed. The constructed HE5cT-Rd19-RGD/scIL-12/shc-met plasmid DNA was mixed with a PPCBA-PEI-Arginine (PPA) polymer, thereby constructing a pDNA/PPA polymer complex.

Manufacturing Example 2. Construction of Recombinant Oncolytic Adenovirus Expressing IL-12 and/or shc-met To investigate antitumor effects and antitumor immune response due to an anticancer adenovirus co-expressing IL-12 and shc-met, an anticancer adenovirus was constructed (FIG. 4, distinguishingly marked as HscIL-12 and Hshc-met when the recombinant adenovirus included a human-derived sequence):

HE5cT-Rd19-RGD: Ad vector not containing an expression gene

HE5cT-Rd19-RGD/scIL-12: Ad vector expressing only IL-12

HE5cT-Rd19-RGD/shc-met: Ad vector expressing shRNA for C-Met gene

HE5cT-Rd19-RGD/scIL-12/shc-met: Ad vector expressing shRNA for IL-12 and C-Met gene More particularly, genes respectively expressing human-derived IL-12 p35 (SEQ ID NO: 1) and IL-12 p40 (SEQ ID NO: 2) were respectively inserted into HE5cT-Rd19-RGD. In addition, shRNA of the sequence of SEQ ID NO: 12 which targets 1987th to 2007th nucleotides of mRNA of the human C-met of SEQ ID NO: 10 as a target sequence (SEQ ID NO: 13) was inserted into a recombinant adenovirus vector.

In addition, in the same manner as in the above, each gene respectively expressing mouse-derived IL-12 p35 (SEQ ID NO: 8) and IL-12 p40 (SEQ ID NO: 9) and a shc-met-expressing sequence (SEQ ID NO: 14) targeting 4398th to 4422th nucleotides of the mouse-derived C-MET gene of SEQ ID NO: 11 as a target sequence (SEQ ID NO: 15) and binding complementarily to the nucleotides to inhibit expression thereof were inserted to manufacture an adenovirus vector co-expressing IL-12 and shcmet.

Manufacturing Example 3. Animal Model Establishment 3-1. Human Xenograft Lung Cancer Tumor Model When a nude mouse purchased from Orient was 6-8 weeks old, the human lung cancer cell line (H1975) was injected subcutaneously at $3 \times 10^6$ cells/50 μL into the nude mouse. Next, when the size of tumor reached an average of 100 mm³, the anticancer adenovirus of Preparation Example 1 or 2 was administered thereto, and the effect thereof was confirmed.

3-2. Mouse Tumor Model

For experiments, C57BL6 (B16-F10 tumor model) mice were purchased from Daehan Biolink, and BALB/C (CT26 tumor model) mice were purchased from Orient. When mice were 6-8 weeks old, a mouse skin cancer cell line (B16-F10) or a mouse gastric cancer cell line (CT26) was injected subcutaneously into a mouse at $5 \times 10^5$ cells/50 μL, and then, when the size of tumor reached an average of 100 mm³, the anticancer adenovirus of Manufacturing Example 1 or 2 was administered and the effects thereof were confirmed.

Experimental Example 1. Confirmation of Expression of mIL-12 and hIL-12 in Cells by Ad pDNA To investigate the expression of the human IL-12 (hIL-12) gene by Ad pDNA constructed according to Manufacturing Example 1, mT-Rd19-RGD and mT-Rd19-RGD/hIL-12/shc-met Ad pDNA were reacted with lipofectamine at room temperature, and then 50% confluent 293A, which is a human embryonic kidney cell line with good intracellular delivery efficiency, was reacted with the reaction product. At 72 hours after treatment, the cell culture medium was collected to perform hIL-12 ELISA.

As shown in FIG. 2, it was confirmed that, in the case of the example (mT-Rd19-RGD/hIL-12/shc-met Ad pDNA; two Pac I), hIL-12 was expressed at 97,500±6,384 pg/mL. Accordingly, it was confirmed that Ad pDNA constructed according to the example efficiently induced the expression of the therapeutic gene, interleukin-12, in cells.

Experimental Example 2. Confirmation of Co-Expression of Intercellular IL-12 and C-met by Adenovirus (Ad) pDNA In consideration of the intracellular delivery efficiency of the adenovirus pDNA constructed according to Manufacturing Example 1, the expression of hIL-12 by mT-Rd19-RGD/hIL-12/shc-met Ad pDNA was investigated in the 293A cell line. However, C-met expression inhibition by the expression of C-met-specific shRNA was not confirmed in the 293A cell line because C-met was not over-expressed in normal 293A cells.

Accordingly, to verify the C-met expression inhibition ability by mT-Rd19-RGD/hIL-12/shc-met (two Pac I) of the example, mT-Rd19-RGD/hIL-12/shc-met adenovirus (Ad) was manufactured, a 50%-confluent human lung cancer cell line A549 overexpressing C-met in a 6-well plate was treated with 20 μl of the manufactured mT-Rd19-RGD/hIL-12/shc-met adenovirus (Ad). At 48 hours after the treatment, the cell culture medium was collected and ELISA for hIL-12 and C-met was performed. The expression amounts of hIL-12 and C-met in a non-treated A549 human lung cancer cell line were used as controls.

As shown in FIG. 3, it was confirmed that the expression (235,000±20,518 pg/mL) of hIL-12 by mT-Rd19-RGD/hIL-12/shc-met Ad increased compared to the control, and the expression of C-met in the group treated with mT-Rd19-RGD/hIL-12/shc-met Ad was reduced by 1.2 times, compared to the control. Accordingly, it can be confirmed that the expression of the therapeutic genes, IL-12 and shc-met, is efficiently induced by the Ad system manufactured according to the present invention.

Experimental Example 3. Confirmation of In-Vivo Antitumor Effects of Anticancer Adenovirus Co-Expressing IL-12 and shc-met (Mouse Syngeneic Tumor Model)

To verify the anticancer treatment effect of the anticancer adenovirus, which co-expressed mouse IL-12 and mouse C-met-targeting shc-met, constructed according to Manufacturing Example 2, respective tumor models were established using the mouse skin cancer cell line B16-F10 or the mouse gastric cancer cell line CT26, and antitumor effects were confirmed.

After subcutaneously injecting the mouse skin cancer cell line B16-F10 or the mouse gastric cancer cell line CT26 at $5\times10^5$ cells/50 µL into mice, PBS or HE5cT-Rd19-RGD/scIL-12/shc-met was respectively injected into the mice when the size of tumor reached an average of 100 mm$^3$. After administration into the tumor three times at intervals of two days ($1\times10^{10}$ VP), the size of the tumor was measured to observe the antitumor effect.

As shown in FIGS. 5a and 5b, it was confirmed that, using two types of mouse tumor models, tumors grew rapidly in the PBS-treated group, but tumors completely disappeared in all subjects administered HE5cT-Rd19-RGD/scIL-12/shc-met.

Experimental Example 4. Confirmation of In-Vivo Antitumor Effects of Anticancer Adenovirus pDNA/PPA Complex Co-Expressing IL-12 and shc-met (Mouse Syngeneic Tumor Model)

A complex (pDNA/PPA) of HE5cT-Rd19-RGD/scIL-12/shc-met viral DNA) and PPA polymer constructed according to Manufacturing Examples 1 to 2 was constructed to confirm the anticancer treatment effect. Particularly, tumor models were established using the mouse skin cancer cell line B16-F10, and the antitumor effects therein were confirmed. The mouse skin cancer cell line (B16-F10) was subcutaneously injected at $5\times10^5$ cells/50 µL into mice, and then, when the size of tumor reached an average of 100 mm$^3$, PBS and the HE5cT-Rd19-RGD/scIL-12/shc-met Ad pDNA/PPA complex were respectively injected into the mouse models. After administration into the tumor 7 times daily, the size of the tumor was measured to observe the antitumor effect.

As shown in FIG. 6, it was confirmed that the size of tumor increased up to 2514.7±202.1 mm$^3$ in the PBS-administered group, whereas significant antitumor effects were exhibited in all subjects of the group administered the anticancer virus, pDNA/PPA complex. The average tumor size in the group administered HE5cT-Rd19-RGD/scIL-12/shc-met Ad pDNA/PPA complex was 1387.6±171.8 mm$^3$, which is 44.8% lower compared to the PBS-administered group. This result indicates that the viral DNA co-expressing IL-12 and shc-met also induces improved antitumor effects.

Experimental Example 5. Confirmation of Intercellular Expression of IL-12 and shc-met by Anticancer Adenovirus Co-Expressing IL-12 and shc-met (Human)

To investigate the expression of human IL-12 or human c-Met-targeting shc-Met by the anticancer adenovirus co-expressing IL-12 and shc-met, the human lung cancer cell line H1975 was administered each of the recombinant adenoviruses HE5cT-Rd19-RGD, HE5cT-Rd19-RGD/shc-met, HE5cT-Rd19-RGD/hscIL-12 and HE5cT-Rd19-RGD/hscIL-12/shc-met constructed according to Manufacturing Example 2 at 2 MOI (FIG. 7b) or 5 MOI (FIG. 7a). At 48 hours after the treatment, the cells and the culture medium were collected to perform ELISA for human IL-12 and western blotting for c-Met and to confirm the expression of each gene.

As shown in FIG. 7a, it was confirmed that human IL-12 was expressed in both HE5cT-Rd19-RGD/hscIL-12 (3066.3±165.7 pg/mg) and HE5cT-Rd19-RGD/hscIL-12/shc-met (94922.6±185.8 pg/mg) recombinant vectors.

In addition, as shown in FIG. 7b, it was confirmed that, in the cells treated with the HE5cT-Rd19-RGD/shc-met or HE5cT-Rd19-RGD/hscIL-12/shc-met recombinant vector, the expression of C-met was inhibited, compared to the HE5cT-Rd19-RGD control. Accordingly, it was confirmed that the expression of the therapeutic genes IL-12 and shc-met inserted into the recombinant anticancer adenovirus vector manufactured in the present invention was efficiently induced.

Experimental Example 6. Verification of Cancer Cell Killing Ability of Anticancer Adenovirus Co-Expressing Human-Derived IL-12 and shc-met To investigate the cancer cell killing ability of the anticancer adenovirus co-expressing human-derived IL-12 and shc-met, the human lung cancer cell line H1975 was infected with the anticancer adenovirus HE5cT-Rd19-RGD; HE5cT-Rd19-RGD/hscIL-12; HE5cT-Rd19-RGD/shc-met; or HE5cT-Rd19-RGD/hscIL-12/shc-met manufactured according to Manufacturing Example 2 at 2, 5, 10, 20, or 50 MOI, and the cancer cell killing ability of the adenovirus was observed under a normal oxygen condition (normoxia) and hypoxia condition (hypoxia).

As shown in FIGS. 8a and 8b, it was confirmed that the cancer cell killing ability of HE5cT-Rd19-RGD, HE5cT-Rd19-RGD/hscIL-12, HE5cT-Rd19-RGD/shc-met, or HE5cT-Rd19-RGD/hscIL-12/shc-met increased in proportion to virus titer under both a normal oxygen condition and a hypoxia condition. In addition, under the 50 MOI-infected conditions, the cancer cell killing ability of the group treated with a single therapeutic gene, i.e., HE5cT-Rd19-RGD/hscIL-12 or HE5cT-Rd19-RGD/shc-met, increased compared to HE5cT-Rd19-RGD, but the co-expression group, i.e., HE5cT-Rd19-RGD/hscIL-12/shc-met, induced remarkably increased cancer cell killing ability, compared to the single-treated group. This result indicates that co-expression of IL-12 and shc-met exhibits a synergistic effect in chemotherapy.

Experimental Example 7. Verification of Ability of Anticancer Adenovirus Co-Expressing Human-Derived IL-12 and shc-met to Inhibit a Migration and Invasion of HUVEC HGF expressed in cancer cells has been reported to increase the migration and invasion of cancer cells by activating the C-met signaling system in vascular endothelial cells, and to induce abnormal blood vessel formation as a result. Therefore, the following experiment was conducted to confirm whether the anticancer adenovirus co-expressing IL-12 and shc-met can reduce the metastasis and invasive ability of HUVEC.

The human lung cancer cell line H1975 was infected with HE5cT-Rd19-RGD, HE5cT-Rd19-RGD/hscIL-12, HE5cT-Rd19-RGD/shc-met, or HE5cT-Rd19-RGD/hscIL-12/shc-met, and then a supernatant was collected to preform migration and invasion assay. As controls, a non-treated medium (fresh media, 5% FBS RPMI) and a cancer cell medium (H1975-culture media, H1975-CM) not injected with an anticancer virus were used.

As shown in FIGS. 9a, 9b, 9c and 9d, it was confirmed that the migration and invasion ability of HUVEC in H1975-

CM (cancer cell medium not infected with anticancer virus) increased, compared to the group treated with a non-treated medium (fresh media). On the other hand, it was confirmed that, in the group of cancer cells that were treated with a medium infected with HE5cT-Rd19-RGD/HscIL-12 or HE5cT-Rd19-RGD/Hshc-met, the migration and invasion ability of HUVEC was reduced compared to the group infected with HE5cT-Rd19-RGD, particularly, the migration and invasion ability of HUVEC was remarkably inhibited in the cancer cell medium infected with HE5cT-Rd19-RGD/HscIL-12/Hshc-met. These results indicate that the amount of HGF expressed in cancer cells is efficiently inhibited by the anticancer adenovirus co-expressing IL-12 and she-met, resulting in a synergetic effect in reducing the migration and invasion ability of HUVEC.

Experimental Example 8. Confirmation of Epithelial-Mesenchymal Mutation (Endo-MT) Inhibition Effect of Anticancer Adenovirus Co-Expressing Human-Derived IL-12 and shc-met To verify the blood vessel normalization effect induced by the anticancer adenovirus co-expressing IL-12 and she-met, H1975 the human lung cancer cell line was infected with HE5cT-Rd19-RGD, HE5cT-Rd19-RGD/HscIL-12, HE5cT-Rd19-RGD/Hshc-met, or HE5cT-Rd19-RGD/HscIL-12/Hshc-met, and then a supernatant was collected therefrom. HUVEC cells were cultured in the supernatant, and then changes in the expression of endothelial or mesenchymal markers were investigated through western blot. As controls, a non-treated medium (fresh media, 5% FBS RPMI), and a cancer cell medium not infected with an anticancer virus were used.

As shown in FIG. 10, it was confirmed that, in the case of the groups treated with the culture medium that was collected from the cancer cells infected with HE5cT-Rd19-RGD/Hshc-met or HE5cT-Rd19-RGD/HscIL-12/Hshc-met, the expression of mesenchymal markers, N-cadherin and a-SMA, was reduced, compared to the control (fresh media-treated group). Thereamong, the group treated with the adenovirus co-expressing IL-12 and shc-met exhibited the most excellent expression reduction effect. These results indicate that co-expression of IL-12 and she-met not only inhibits the migration and invasion ability of HUVEC cells, but also inhibits endo-MT transition, thereby exhibiting excellent blood vessel renormalization effect.

Experimental Example 9. Confirmation of In Vivo Antitumor Effects of Anticancer Adenovirus Co-Expressing IL-12 and shc-met in Human Xenograft Tumor Model To verify the anticancer treatment effect of the anticancer adenovirus of the present invention co-expressing IL-12 and she-met in a human xenograft tumor model, tumor models were established using the human lung cancer cell line H1975, and antitumor effects therein were investigated.

To establish the human xenograft tumor models, particularly, the human lung cancer cell line (H1975) at $3 \times 10^6$ cells/50 µL was subcutaneously injected into nude mice, and then, when the tumor size reached an average of 100 mm$^3$, PBS, HE5cT-Rd19-RGD, HE5cT-Rd19-RGD/HscIL-12, HE5cT-Rd19-RGD/Hshc-met, and HE5cT-Rd19-RGD/HscIL-12/Hshc-met were respectively administered. After administration ($5 \times 10^6$ pfu) into the tumor twice every two days, the tumor size was measured.

As shown in FIG. 11, it was confirmed that tumors rapidly proliferated in the PBS-administered group, but significant antitumor effects were observed in all of the groups administered with the anticancer adenovirus. Particularly, it can be confirmed that, compared to the PBS-administered group, the tumor size is reduced by 81.7% in HE5cT-Rd19-RGD, 85.5% in HE5cT-Rd19-RGD/HscIL-12, 92.2% in HE5cT-Rd19-RGD/Hshc-met, and 94.6% in HE5cT-Rd19-RGD/HscIL-12/Hshc-met. From these results, it can be confirmed that, when the anticancer adenovirus co-expressing IL-12 and she-met is used, synergistic effects can be provided, compared to the single-treated group.

Experimental Example 10. Confirmation of IL-12 Expression and C-met Expression Reduction in Cells by Anticancer Adenovirus Co-Expressing IL-12 and Lbcpf1-crMET

Experimental Example 10-1. Construction of Anticancer Adenovirus Co-Expressing IL-12 and C-met-Targeting CRISPR RNA CRISPR RNA system (LbCpf1-crRNA system) was constructed using 3.5 generation gene scissors (CRISPR/Cpf1) that allows gene correction and desired mutation to occur in the process of cutting a target DNA, and then reconnecting the same through an intracellular repair system, so as to investigate whether the same effect is exhibited when the CRISPR system is used in the adenovirus system of the present invention. IL-12 sequence was located in a recombinant vector in the same manner as in Manufacturing Example 2, but the sequence (SEQ ID NO: 6) (indicated as HIL-12 in FIG. 12) comprising an IRES coding sequence (SEQ ID NO: 20) was disposed between the sequence encoding p35 of IL-12 (SEQ ID NO: 4) and the sequence encoding p40 of IL-12 (SEQ ID NO: 5).

C-met target guide RNA sequences were selected using a program, and then oligomer synthesis was commissioned by Bionics. Cloning was performed through annealing. The gene encoding Cpf1 protein (SEQ ID NO: 18) was inserted into the E1 site of RdB-RGD adenovirus, and the U6 promoter was positioned upstream of a site expressing guide RNA (crC-met). In addition, the sequence encoding IL-12; and the sequence expressing C-met-targeting guide RNA (SEQ ID NO: 16) were inserted into the E3 region of RdB-RGD adenovirus, thereby constructing a recombinant adenovirus that co-expresses IL-12 and the CRISPR-CAS system. The guide RNA was designed to target the 55th to 77th nucleotides of the human C-met sequence of SEQ ID NO: 10 (FIG. 12).

It was confirmed that, when the guide RNA (crcmet) expressed by the constructed recombinant adenovirus recognizes a target site of a target gene and designates a position to be corrected, the gene scissors Cpf1 can cut a target site and thus can efficiently inhibit C-met.

Experimental Example 10-2. Investigation of C-met Inhibition Effect Due to Anticancer Adenovirus Co-Expressing IL-12 and C-met-Targeting CRISPR RNA To investigate the expression of human-derived IL-12 or C-met expression reduction through Lbcpf1-crMET system, due to the anticancer adenovirus co-expressing IL-12 and Lbcpf1-crMET, the human lung cancer cell line H1975 was infected with the anticancer adenovirus at 5 MOI or 100

MOI, and after 48 hours, cells and culture media were collected and subjected to ELISA for human IL-12 or western blot for c-Met.

As shown in FIGS. 13*a*, 13*b*, and 13*c*, IL-12 expressions of 9000.0±600.0 pg/mL and 17400.0±1200.0 pg/mL were respectively confirmed in the groups respectively treated with RdB-RGD/Lbcpf1/HscIL-12 and RdB-RGD/Lbcpf1/HscIL-12-crMET. In addition, it was confirmed that the expression of C-met was inhibited in all of the groups treated with the anticancer virus. Particularly, the expression of C-met was most efficiently reduced by RdB-RGD/Lbcpf1/HscIL-12-crMET.

Experimental Example 11. Confirmation of In Vivo Antitumor Effects of Anticancer Adenovirus Co-Expressing IL-12 and Lbcpf1-crMET in Human Xenograft Tumor Models Experiments were conducted to investigate whether C-met expression inhibition by CRISPR, not shRNA, can be realized together the expression of IL-12 in human xenograft tumor models.

C-met expression inhibition by CRISPR was investigated using the Lbcpf1-crMET system constructed according to Experimental Example 10-1.

To verify the anticancer treatment effect of the anticancer adenovirus co-expressing IL-12 and Lbcpf1-crMET, tumor models were established using the human lung cancer cell line H1975 and antitumor effects therein were investigated. The human lung cancer cell line H1975 was subcutaneously injected at $3 \times 10^6$ cells/50 μL into nude mice, and then, when the tumor size reached an average of 90 mm$^3$, PBS, RdB-RGD/Lbcpf1, RdB-RGD/Lbcpf1/HscIL-12, and RdB-RGD/Lbcpf1/HscIL-12-crMET were respectively administered. After administration ($5 \times 10^6$ VP) into the tumor three times every two days, the tumor size was measured to observe antitumor effects.

As shown in FIG. 14, the tumor size rapidly increased to 1486.5±221.1 mm$^3$ on the 25$^{th}$ days in the PBS-administered group, but a significant antitumor effect was observed in all of the groups treated with the anticancer virus. In the groups treated with the anticancer virus, an average of tumor size was 876.9±146.2 mm$^3$ (RdB-RGD/Lbcpf1), 792.0±230.3 mm$^3$ (RdB-RGD/Lbcpf1/scIL-12), and 535.6±172.6 mm$^3$ (RdB-RGD/Lbcpf1/scIL-12-crMET), respectively. That is, in the groups treated with the anticancer virus, the size of tumor was 41.0, 46.7 or 64% reduced, compared to the PBS-administered group. Particularly, in the case in which the CRISPR method was used to be co-expressed with IL-12, the tumor size was remarkably reduced. Therefore, it was confirmed that the synergistic effect due to the two therapeutic genes was exhibited also when the CRISPR system was used.

The invention claimed is:

1. A recombinant oncolytic adenovirus comprising a first heterologous gene and a second heterologous gene;
   wherein the first heterologous gene encodes interleukin-12 (IL-12); and
   wherein the second heterologous gene encodes an oligonucleotide that is complementary to mRNA of C-met and inhibits expression of C-met, wherein the oligonucleotide that is complementary to mRNA of C-met is selected the group consisting of small hairpin RNA (shRNA), siRNA, antisense oligonucleotides, and guide RNA for CRISPR.

2. The recombinant oncolytic adenovirus according to claim 1, wherein the first heterologous gene encoding interleukin-12 (IL-12) comprises an IL-12A (p35) gene sequence and an IL-12B (p40) gene sequence.

3. The recombinant oncolytic adenovirus according to claim 1, wherein the first heterologous gene encoding interleukin-12 (IL-12) further comprises a linker sequence or internal ribosome entry site (IRES) sequence between the IL-12A (p35) gene sequence and the IL-12B (p40) gene sequence.

4. The recombinant oncolytic adenovirus according to claim 1, wherein the first heterologous gene encoding interleukin-12 (IL-12) is inserted into an E1B region of the recombinant oncolytic adenovirus.

5. The recombinant oncolytic adenovirus according to claim 1, wherein the second heterologous gene expressing an oligonucleotide that is complementary to mRNA of C-met is inserted into an E1B region of the recombinant oncolytic adenovirus.

6. The recombinant oncolytic adenovirus according to claim 1,
   wherein, when the oligonucleotide complementarily binding to the C-met gene to inhibit expression of C-met is a guide RNA for CRISPR,
   wherein the recombinant oncolytic adenovirus further comprises a nucleotide sequence expressing Cas protein.

7. The recombinant oncolytic adenovirus according to claim 1, further comprising a biocompatible polymer in a form of being combined with the recombinant oncolytic adenovirus.

8. The recombinant oncolytic adenovirus according to claim 7, wherein the biocompatible polymer is selected from the group consisting of PEI-Arg-mPEG-S-S-mPEG-Arg-PEI (PAPS), mPEG-PEI-g-Arg-S-S-Arg-g-PEI-mPEG (PPSA), pegylated and iron oxide nanoparticles-crosslinked catechol-grafted poly L lysine (PICION), an arginine-grafted biodegradable polymer (ABP), a pegylated and PTX-conjugated polymeric micelle (APP), mPEG-b-Pip-CBA (PPCBA), PPCBA-PEI-Arginine (PPA), poly(amido-amine) dendrimer (PAMAM), polyethyleneglycol (PEG), poly-lactide (PLA), polyglycolide (PGA), poly-lactide-co-glycolide (PLGA), poly-ε-caprolactone (PCL), polyethylenimine (PEI), hyaluronic acid (HA), gelatin, chitosan, and serum albumin.

9. A method for treating cancer, comprising administering a therapeutically effective amount of an adenovirus system according to claim 1 to a subject.

10. The method for treating cancer according to claim 9, wherein the cancer is gastric cancer, lung cancer, non-small cell lung cancer, breast cancer, ovarian cancer, liver cancer, bronchial cancer, nasopharyngeal cancer, laryngeal cancer, pancreatic cancer, bladder cancer, colorectal cancer, colon cancer, cervical cancer, bone cancer, non-small cell bone cancer, blood cancer, skin cancer (melanoma etc.), head or neck cancer, uterine cancer, rectal cancer, anal cancer, colon cancer, fallopian tube cancer, endometrial cancer, vaginal cancer, vulvar cancer, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, kidney or ureter cancer, renal cell carcinoma, renal pelvic carcinoma, poly-ploid carcinoma, salivary gland cancer, sarcoma cancer, pseudomyxoma, hepatoblastoma, testicular cancer, glioblastoma, cleft lip cancer, ovarian germ cell tumor, basal cell carcinoma, multiple myeloma, gallbladder cancer, choroidal melanoma, ampulla of vater cancer, peritoneal cancer, adrenal cancer, tongue cancer, small cell cancer, pediatric lymphoma, nerve blastoma, duodenal cancer, ureteral cancer, astrocytoma, meningioma, renal carcinoma, vulvar cancer, thymus cancer, central nervous system (CNS) tumor, primary central nervous system lymphoma, spinal cord tumor, brain stem glioma, or pituitary adenoma.

11. The method for treating cancer according to claim 9, wherein the composition is intratumorally administered.

12. A method for enhancing antitumor immunity, comprising administering a therapeutically effective amount of an adenovirus system according to claim 1 to a subject.

13. The method for enhancing antitumor immunity according to claim 12, wherein the composition is intratumorally administered.

* * * * *